(12) United States Patent
Roger et al.

(10) Patent No.: US 11,786,273 B2
(45) Date of Patent: *Oct. 17, 2023

(54) SPINAL ALIGNMENT AND SECUREMENT

(71) Applicant: Spinal Developments Pty Ltd, North Sydney (AU)

(72) Inventors: Gregory James Roger, Milsons Point (AU); Davor Saravanja, Roseville (AU)

(73) Assignee: SPINAL DEVELOPMENTS PTY LTD., North Sydney (AU)

( * ) Notice: Subject to any disclaimer, the term of this patent is extended or adjusted under 35 U.S.C. 154(b) by 353 days.

This patent is subject to a terminal disclaimer.

(21) Appl. No.: 17/139,082

(22) Filed: Dec. 31, 2020

(65) Prior Publication Data
US 2021/0220019 A1 Jul. 22, 2021

Related U.S. Application Data

(63) Continuation of application No. 16/184,001, filed on Nov. 8, 2018, now Pat. No. 10,905,470, which is a (Continued)

(30) Foreign Application Priority Data

Oct. 9, 2014 (AU) .................. 2014904032
Nov. 10, 2014 (AU) .................. 2014904536

(51) Int. Cl.
*A61B 17/70* (2006.01)
*A61B 17/68* (2006.01)

(52) U.S. Cl.
CPC ...... *A61B 17/7043* (2013.01); *A61B 17/7032* (2013.01); *A61B 17/7037* (2013.01); *A61B 17/7049* (2013.01); *A61B 2017/681* (2013.01)

(58) Field of Classification Search
CPC . A61B 17/70; A61B 17/7019; A61B 17/7022; A61B 17/7049–7053
See application file for complete search history.

(56) References Cited

U.S. PATENT DOCUMENTS 4,269,178 A 5/1981 Keene
4,361,141 A 11/1982 Tanner
(Continued)

FOREIGN PATENT DOCUMENTS

DE 2834891 A1 1/1980
EP 0565149 A2 10/1993
(Continued)

OTHER PUBLICATIONS

"CD Horizon Legacy Spinal System", MEDTRONIC, <http://www.medtronic.com/us-en/patients/treatments-therapies/spinal-fusion-scoliosis-surgery/cd-horizon-legacy-system.html> (2017).
(Continued)

*Primary Examiner* — Eduardo C Robert
*Assistant Examiner* — Michelle C Eckman
(74) *Attorney, Agent, or Firm* — Browdy and Neimark, PLLC

(57) ABSTRACT

A surgical connection device for a spine is disclosed including a stabilization member, compression arms and traction arms, the device being used in conjunction with first anchor points fixed to vertebrae at a first lateral side of the spine and second anchor points fixed to vertebrae at a second lateral side of the spine. A first spinal rod may be attached to the first anchor points and a second spinal rod may be attached to the second anchor points. The compression arms connect the stabilization member to the first and second anchor points or rods and bear compressive forces. The traction arms connect the stabilization member to the first and o second anchor points or rods and bear tensile forces. Appli-
(Continued)

cation of both tensile and compressive forces via the device may serve to straighten, change a direction of bending or increase a degree of bending of the rods and/or spine. The use of the traction arms may also provide for a more flexible construct.

23 Claims, 14 Drawing Sheets

Related U.S. Application Data continuation of application No. 15/517,775, filed as application No. PCT/AU2015/050615 on Oct. 9, 2015, now Pat. No. 10,143,498.

(56) References Cited

U.S. PATENT DOCUMENTS

| | | |
|---|---|---|
| 4,773,402 A | 9/1988 | Asher |
| 5,380,325 A | 1/1995 | Lahille et al. |
| 5,381,212 A | 1/1995 | Noguchi |
| 5,382,248 A | 1/1995 | Jacobson |
| 5,437,669 A | 8/1995 | Yuan |
| 5,466,238 A | 11/1995 | Lin |
| 5,531,747 A | 7/1996 | Ray |
| 5,702,392 A | 12/1997 | Wu |
| 5,702,452 A | 12/1997 | Argenson et al. |
| 6,325,802 B1 | 12/2001 | Frigg |
| 6,755,828 B2 | 6/2004 | Shevtsov |
| 6,872,208 B1 | 3/2005 | McBride et al. |
| 7,220,262 B1 | 5/2007 | Hynes |
| 7,294,129 B2 | 11/2007 | Hawkins et al. |
| 7,473,269 B1 | 1/2009 | Hynes |
| 7,686,833 B1 | 3/2010 | Muhanna et al. |
| 7,947,066 B2 | 5/2011 | Tepper et al. |
| 8,043,338 B2 | 10/2011 | Dant |
| 8,177,814 B2 | 5/2012 | Predick |
| 8,241,334 B2 | 8/2012 | Butler et al. |
| 9,757,157 B2 | 9/2017 | Seme |
| 9,888,945 B2 | 2/2018 | Walters |
| 9,895,174 B2 | 2/2018 | Ozdil |
| 2004/0236328 A1 | 11/2004 | Lee |
| 2004/0260287 A1 | 12/2004 | Ye-Kui |
| 2005/0119748 A1 | 6/2005 | Reiley et al. |
| 2006/0079896 A1 | 4/2006 | Kwak et al. |
| 2006/0149230 A1 | 7/2006 | Kwak et al. |
| 2006/0149244 A1 | 7/2006 | Amrein et al. |
| 2006/0282077 A1* | 12/2006 | Labrom ............ A61B 17/7043 606/279 |
| 2006/0282079 A1 | 12/2006 | Labrom |
| 2007/0073289 A1 | 3/2007 | Kwak |
| 2007/0088359 A1* | 4/2007 | Woods ............... A61B 17/7049 606/86 A |
| 2007/0173828 A1 | 7/2007 | Firkins |
| 2007/0191831 A1 | 8/2007 | Sanders |
| 2007/0233090 A1* | 10/2007 | Naifeh ............... A61B 17/7052 606/258 |
| 2009/0234390 A1 | 9/2009 | Poirier |
| 2009/0318968 A1 | 12/2009 | Duggal et al. |
| 2010/0137911 A1* | 6/2010 | Dant ................. A61B 17/7043 606/252 |
| 2010/0262196 A1 | 10/2010 | Barrus et al. |
| 2011/0066188 A1 | 3/2011 | Seme et al. |
| 2012/0078303 A1 | 3/2012 | Malek |
| 2012/0078305 A1* | 3/2012 | Wang ................ A61B 17/7059 606/257 |
| 2012/0095510 A1 | 4/2012 | Nihalani |
| 2012/0095511 A1* | 4/2012 | Nihalani ........... A61B 17/7004 606/264 |
| 2012/0095512 A1* | 4/2012 | Nihalani ........... A61B 17/7004 606/251 |
| 2012/0150230 A1* | 6/2012 | Felix ................. A61B 17/7052 606/250 |
| 2012/0158064 A1 | 6/2012 | Kroll |
| 2013/0090691 A1 | 4/2013 | Zhang |
| 2013/0184762 A1 | 7/2013 | Harper et al. |
| 2014/0277146 A1* | 9/2014 | Li ..................... A61B 17/7052 606/252 |
| 2015/0182263 A1 | 7/2015 | Donner |
| 2016/0302929 A1 | 10/2016 | Freese |
| 2017/0095278 A1 | 4/2017 | Zhang |
| 2017/0119439 A1* | 5/2017 | Ozdil ................. A61B 17/701 |
| 2017/0189072 A9 | 7/2017 | Walters |
| 2017/0231661 A1* | 8/2017 | Bannigan .......... A61B 17/7043 606/263 |
| 2017/0238971 A1 | 8/2017 | Roger |
| 2017/0325852 A1 | 11/2017 | Chen |
| 2018/0008323 A1 | 1/2018 | Donner |
| 2018/0049778 A1 | 2/2018 | Lemerovich |
| 2018/0070993 A1 | 3/2018 | Leff |
| 2018/0070994 A1 | 3/2018 | Leff |
| 2019/0216507 A1 | 7/2019 | Bannigan |

FOREIGN PATENT DOCUMENTS

| | | |
|---|---|---|
| FR | 2713473 A1 | 6/1995 |
| FR | 2804314 A1 | 8/2001 |
| GB | 2479829 A | 10/2011 |
| WO | 2009055407 A1 | 4/2009 |
| WO | 2015142320 A1 | 9/2015 |

OTHER PUBLICATIONS

"MESA® Deformity Spinal System", K2M, Inc. <http://www.k2m.com/products/product/mesa-deformity/> (2018).
"The BIOSPINE", bio-spine.com <http://www.bio-spine.com/about.htm> (2018).
"DSS® Stabilization System", Paradigm Spine, <http://www.paradigmspine.com/content/dss-stabilization-system/>, (2015).
European Search Report for corresponding EP 15 84 9272 dated May 23, 2018.

* cited by examiner

SPINAL ALIGNMENT AND SECUREMENT

CROSS-REFERENCE TO RELATED APPLICATIONS

The present application claims priority from Australian Provisional Patent Application No 2014904032 filed on 9 Oct. 2014 and Australian Provisional Patent Application No 2014904536 filed on 10 Nov. 2014, the contents of which are incorporated herein by reference.

TECHNICAL FIELD

The present disclosure relates to posterior spinal surgery and devices used in spinal surgery.

BACKGROUND

Posterior spinal surgery, including spinal fixation surgery, is a common procedure used in the treatment of spinal conditions such as spondylolisthesis, scoliosis, spinal trauma, spinal tumor and other spinal deformities or degenerative conditions.

Typically, the surgery involves inserting pedicle screws into vertebrae to establish anchor points. A stabilizing rod may then be secured between several of the anchor points to restrict or limit relative movement between vertebrae. This process can be carried out on opposite sides of the spine, such as to secure two stabilizing rods to the spine. To further stabilize the spine, a connection device can be applied between the two stabilizing rods or between the anchor points (e.g. when no stabilizing rods are used), maintaining the position of the rods and/or anchor points relative to each other. When the posterior spinal fixation surgery is completed, spinal fusion may be carried out.

An example of a connection device applied between stabilizing rods is disclosed in patent publication US 2012/0095510 A1.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to one aspect, the present disclosure provides a surgical connection device for a spine, a plurality of first anchor points being fixed to vertebrae at a first lateral side of the spine, a plurality of second anchor points being fixed to vertebrae at a second lateral side of the spine, a first spinal rod being attached to the plurality of first anchor points and a second spinal rod being attached to the plurality of second anchor points, the device comprising:
  a stabilization member;
  a plurality of compression arms to connect the stabilization member to the first and second rods and bear compressive forces between the stabilization member and the first and second rods; and
  a plurality of traction arms to connect the stabilization member to the first and second rods and bear tensile forces between the stabilization member and the first and second rods.

According to another aspect, the present disclosure provides a surgical connection device for a spine, a plurality of first anchor points being fixed to vertebrae at a first lateral side of the spine and a plurality of second anchor points being fixed to vertebrae at a second lateral side of the spine, the device comprising:
  a stabilization member;
  a plurality of compression arms to connect the stabilization member to at least one first anchor point and at least one second anchor point and bear compressive forces between the stabilization member and the first and second anchor points; and
  a plurality of traction arms to connect the stabilization member to at least one first anchor point and at least one second anchor point and bear tensile forces between the stabilization member and the first and second anchor points.

According to another aspect, the present disclosure provides a surgical method for a spine, a plurality of first anchor points being fixed to vertebrae at a first lateral side of the spine, a plurality of second anchor points being fixed to vertebrae at a second lateral side of the spine, a first spinal rod being attached to the plurality of first anchor points and a second spinal rod being attached to the plurality of second anchor points, the method comprising:
  connecting a stabilization member of a surgical connection device to the first and second rods using a plurality of compression arms that are configured to bear compressive forces between the stabilization member and the rods; and
  connecting a plurality of traction arms of the surgical connection device between the stabilization member and the first and second rods, the traction arms being configured to bear tensile forces between the stabilization member and the rods.

According to another aspect, the present disclosure provides a surgical method for a spine, a plurality of first anchor points being fixed to vertebrae at a first lateral side of the spine and a plurality of second anchor points being fixed to vertebrae at a second lateral side of the spine, the method comprising:
  connecting a stabilization member of a surgical connection device to at least one first anchor point and at least one second anchor point using a plurality of compression arms that are configured to bear compressive forces between the stabilization member and the first and second anchor points; and
  connecting a plurality of traction arms of the surgical connection device between the stabilization member and at least one first anchor point and at least one second anchor point, the traction arms being configured to bear tensile forces between the stabilization member and the first and second anchor points.

The stabilization member may be elongate. The direction of elongation of the stabilization member may be substantially parallel to the spinal axis. The stabilization member may be rod-like. The stabilization member may comprise one or more rods. When first and second rods are provided attached to anchor points, the stabilization member may provide a third spinal rod, or third and fourth spinal rods, that is/are substantially parallel to the first and second rods. The stabilization member may extend across multiple vertebrae, e.g. at least 2 vertebrae, at least 3 vertebrae or at least 4 vertebrae. Nevertheless, the stabilization member may take a variety of different forms.

The anchor points may be bone screws or other surgical devices that provide means for fixation to vertebrae of the spine. Bone screws may include pedicle screws, for example.

The stabilization member may provide for stiffening of the rods when connected to the rods or provide for stabilizing of the anchor points. The stabilization member may provide an anchor device, relative to which compressive and tensile forces can be applied to the rods and/or anchor points, e.g., such as to force a bend in the rods or to straighten the rods and/or to force relative movement of the anchor points and the attached vertebrae. Additionally or alternatively, the stabilization member may provide for stabilization as part of a motion preservation system.

To aid understanding of the configuration of the connection device, various features of the connection device are described and/or distinguished with reference to an anatomical reference system, including anatomical directions and anatomical planes, for example. In general, anatomical references are indicative of the position and orientation of features of the device when the device is in a deployed, implanted state. For example, where superior and inferior elements of the device are described, it can be expected that the superior element will be located closer to the head of the recipient and the inferior element will be located closer to the feet of the recipient, when the device is in its deployed, implanted state.

The stabilization member may comprise a superior end and an inferior end. The direction of elongation of the stabilization member may extend between the superior and inferior ends. The stabilization member may include walls that extend on opposite sides of the stabilization member between the superior and inferior ends.

The plurality of compression arms may comprise at least a first compression arm to connect between the stabilization member and the first rod or to connect between the stabilization member and a first anchor point, and at least a second compression arm to connect between the stabilization member and the second rod or to connect between the stabilization member and a second anchor point. The first and second compression arms may each have a first end connected to the stabilization member and a second end to connect to the respective rod/anchor point. The first compression arm may be connected to the stabilization member at a position that is on a substantially opposite side of the stabilization member to a position at which the second compression arm is connected to the stabilization member. For example, the first end of the first compression arm may be connected to a first lateral wall of the stabilization member and the first end of the second compression arm may be connected to an opposite second lateral wall of the stabilization member.

The plurality of traction arms may comprise at least two first traction arms to connect between the stabilization member and the first rod/first anchor points and at least two second traction arms to connect between the stabilization member and the second rod/second anchor points. Each of the first and second traction arms may have a first end to connect to the stabilization member and a second end to connect to the respective rod/anchor point. The first traction arms may connect to the stabilization member at a position that is on a substantially opposite side of the stabilization member to a position at which the second traction arms connect to the stabilization member. For example, the first ends of the first traction arms may connect to the first lateral wall of the stabilization member and the first ends of the second traction arms may connect to the second lateral wall of the stabilization member.

The two first traction arms may connect to the first rod at positions on either side of the position at which the first compression arm connects to the first rod. For example, one of the two first traction arms may connect to the first rod at a position that is superior to the position at which the first compression arm connects to the first rod, and the other of the two first traction arms may connect to the first rod at a position that is inferior to the position at which the first compression arm connects to the first rod.

The two first traction arms may therefore pull superior and inferior portions of the first rod towards the stabilization member while the first compression member pushes an intermediate portion of the first rod, between the superior and inferior portions, away from the stabilization member (e.g., to maintain the intermediate portion of the first rod at a fixed distance from the stabilization member). The application of both tensile and compressive forces may serve to straighten the first rod, change a direction of bending of the first rod or increase a degree of bending of the first rod.

Where the plurality of traction arms are connected directly to the anchor points rather than rods, the two first traction arms may connect to two respective first anchor points located either side of a first anchor point to which the first compression arm is connected. For example, one of the two first traction arms may connect to a first anchor point that is superior to the first anchor point to which the first compression arm is connected, and the other of the two first traction arms may connect to a first anchor point at a position that is inferior to the first anchor point to which the first compression arm is connected.

Since the first anchor points can be connected to different vertebrae, the two first traction arms may therefore pull superior and inferior vertebrae towards the stabilization member while the first compression member pushes an intermediate vertebrae, between the superior and inferior vertebrae, away from the stabilization member (e.g., to maintain the intermediate vertebrae at a fixed distance from the stabilization member). The application of both tensile and compressive forces may serve to straighten the spine, change a direction of bending of the spine or increase a degree of bending of the spine. While similar adjustment is described in preceding paragraphs in relation to the first rod, since the first rod is connected to anchor points which can be connected to vertebrae, the adjustment of the first rod may also result in the same spinal adjustment.

Similarly, the two second traction arms may connect to the second rod at positions on either side of the position at which the second compression arm connects to the second rod. For example, one of the two second traction arms may connect to the second rod at a position that is superior to the position at which the second compression arm connects to the second rod, and the other of the two second traction arms may connect to the second rod at a position that is inferior to the position at which the second compression arm connects to the second rod.

The two second traction arms may therefore pull superior and inferior portions of the second rod towards the stabilization member while the second compression member pushes an intermediate portion of the second rod, between the superior and inferior portions, away from the stabilization member (e.g., to maintain the intermediate portion of the second rod at a fixed distance from the stabilization member). The application of both tensile and compressive forces may serve to straighten the second rod, change a direction of bending of the second rod or increase a degree of bending of the second rod.

Where the plurality of traction arms are connected directly to the anchor points rather than two first and second rods, the two second traction arms may connect to two respective second anchor points located either side of a second anchor point to which the second compression arm is connected. For example, one of the two second traction arms may connect to a second anchor point that is superior to the second anchor point to which the second compression arm is connected, and the other of the two second traction arms may connect to a second anchor point at a position that is inferior to the second anchor point to which the second compression arm is connected.

Since the second anchor points can be connected to different vertebrae, the two second traction arms may therefore pull superior and inferior vertebrae towards the stabilization member while the second compression member pushes an intermediate vertebrae, between the superior and inferior vertebrae, away from the stabilization member (e.g., to maintain the intermediate vertebrae at a fixed distance from the stabilization member). The application of both tensile and compressive forces may serve to straighten the spine, change a direction of bending of the spine or increase a degree of bending of the spine. While similar adjustment is described in preceding paragraphs in relation to the rod, since the second rod is connected to anchor points which can be connected to vertebra, the adjustment of the second rod may also result in the same spinal adjustment.

The above described arrangement may draw the rods or spine into lordosis or further lordosis. Where a kyphotic deformity or correction is desired the positions of the compression and traction arms may be reversed. The connection positions of the compression arms to the stabilization member and/or to the rods may be variable along the axes of elongation of the stabilization member and rods. Accordingly, the compression arms may be repositioned along the direction of the spinal axis, to provide compression at a desired point and/or to avoid interfering with the anatomical features or other apparatus, such as pedicle screws. The variability in positioning may also enable a torsional force on the spinal column to be induced or resisted. This may be achieved through locating the compression arms, located at opposite sides of the spine, at different positions along the spinal axis.

Similarly, the connection positions of the traction arms to the stabilization member and/or to the rods may be variable along the axes of elongation of the stabilization member and rods. Accordingly, the traction arms may be repositioned along the direction of the spinal axis, to provide tension at a desired point and/or to avoid interfering with the anatomical features or other apparatus, such as pedicle screws. The variability in positioning may also enable a torsional force on the spinal column to be induced or resisted. This may be achieved through locating the traction arms, located at opposite sides of the spine, at different positions along the spinal axis.

Due to the differing natures of the forces transferred through the compression arms and the traction arms, the compression arms may be configured differently from the traction arms. For example, the compression arms may be rigid elements that can withstand relatively high compression forces without substantially changing shape, e.g., without buckling. The compression arms may be more rigid than the traction arms. The traction arms may be flexible elements. The traction arms may be more flexible than the compression arms but may withstand considerable tensile forces without stretching. In one embodiment, the traction arms are provided by wires or relatively narrow rods, whereas the compression arms are provided by rigid arms that have a width and/or depth that is larger than that of the traction arms. By providing flexible traction arms, e.g., that bend under compression, the surgical connection device may have regions of enhanced flexibility. The traction arms may provide the surgical connection device with spring-like qualities and may enable a degree of "bounce" to take place during its use, in conjunction with the adjacent anatomical structures. This may provide stress protection to the apparatus and adjacent anatomical structures and provide for increased motion preservation of the spine. For example, when the traction arms are provided adjacent inferior and/or superior ends of the surgical connection device, the traction arms may provide a flexible transition between a region of the spine that is stabilized by the connection device and non-stabilized adjacent region(s) of the spine. This may reduce the likelihood of damage, breakage and/or "adjacent segment degeneration" occurring to non-stabilised adjacent regions of the spine, e.g., as a result of force transfer through the connection device and/or stabilized region of the spine. The degree of flexibility of the traction arms, or other arms or connecters disclosed herein, may be selected or tuned to achieve the desired degrees of flexibility or rigidity.

Due to the differing natures of the forces transferred by the compression arms and the traction arms, the manner in which the compression arms connect to the stabilization member and/or rods and/or anchor points may be different to the manner in which the traction arms connect to the stabilization member and/or rods and/or anchor points. The connectors may be connected to the stabilizing member, rods and anchor points using a variety of different techniques.

One or more of the compression and traction arms may extend from the stabilization member in an anterior-lateral direction. Accordingly, when connected to the rods or anchor points, the stabilization member may be located medially and posteriorly of the rods and/or anchor points. Depending on the size of the spine, the stabilization member may be positioned about 5-25 mm posteriorly of a plane extending through the rods or anchor points (e.g. extending through heads of bone screws acting as anchor points) or otherwise.

The stabilization member may be offset from a central axis of the spine, such as to locate laterally of the tips of the spinous processes. Alternatively, when a portion of the spinal lamina and the spinous processes is removed during a laminectomy, the stabilization member may locate along the central axis at a position at or adjacent to the exterior extents of the tips of the spinous processes prior to removal thereof. As another alternative, the stabilization member may comprise two elongate members that each extend along the spine and which are spaced apart in a medial-lateral direction such as to provide a gap to accommodate tips of the spinous processes. The two elongate members may be two rods, for example, which extend substantially parallel to each other on opposite sides of the spinous processes. One or more connectors, e.g. bolts, may connect the elongate members together. The one or more connectors may extend through one or more interspinous spaces between adjacent spinous processes, through one or more interspinous ligaments and/or through one or more spinous processes or any other structure located between the elongate members.

According to one aspect, the present disclosure provides a surgical connection device for a spine, a plurality of first anchor points being fixed to vertebrae at a first lateral side of the spine, a plurality of second anchor points being fixed to vertebrae at a second lateral side of the spine, a first spinal rod being attached to the plurality of first anchor points and a second spinal rod being attached to the plurality of second anchor points, the device comprising:

an elongate stabilization member; and
a plurality of arms to connect the stabilization member to the first and second rods;

wherein the device is configured such that, when the stabilization member is connected to the first and second rods by the plurality of arms, the direction of elongation of the stabilization member lies substantially parallel to the axis of the spine, or other desired axis, and the stabilization member locates:

(a) posteriorly of the rods at a position that is not substantially more posterior than the posterior extents of the tips of spinous processes of the vertebrae to which the anchor points are fixed; or (b) when one or more spinous processes of the vertebrae to which the anchor points are fixed have been removed, posteriorly of the rods at a position that is not substantially more posterior than the positions at which the posterior extents of the tips of the spinous processes of the vertebrae to which the anchor points are fixed were located prior to removal.

According to another aspect, the present disclosure provides a surgical connection device for a spine, a plurality of first anchor points being fixed to vertebrae at a first lateral side of the spine and a plurality of second anchor points being fixed to vertebrae at a second lateral side of the spine, the device comprising:

an elongate stabilization member; and a plurality of arms to connect the stabilization member to the first and second anchor points;

wherein the device is configured such that, when the stabilization member is connected to the first and second anchor points by the plurality of arms, the direction of elongation of the stabilization member lies substantially parallel to the axis of the spine, or other desired axis, and the stabilization member locates:

(a) posteriorly of the anchor points at a position that is not substantially more posterior than the posterior extents of the tips of spinous processes of the vertebrae to which the anchor points are fixed; or (b) when one or more spinous processes of the vertebrae to which the anchor points are fixed have been removed, posteriorly of the anchor points at a position that is not substantially more posterior than the positions at which the posterior extents of the tips of the spinous processes to which the anchor points are fixed were located prior to removal.

According to another aspect, the present disclosure provides a surgical method for a spine, a plurality of first anchor points being fixed to vertebrae at a first lateral side of the spine, a plurality of second anchor points being fixed to vertebrae at a second lateral side of the spine, a first spinal rod being attached to the plurality of first anchor points and a second spinal rod being attached to the plurality of second anchor points, the method comprising:

connecting a stabilization member of a surgical connection device to the first and second rods using a plurality of arms, wherein the connecting locates the stabilization member:

(a) posteriorly of the rods at a position that is not substantially more posterior than the posterior extents of the tips of spinous processes of the vertebrae to which the anchor points are fixed; or (b) when one or more spinous processes of the vertebrae to which the anchor points are fixed have been removed, posteriorly of the rods at a position that is not substantially more posterior than the positions at which the posterior extents of the tips of the spinous processes of the vertebrae to which the anchor points are fixed were located prior to removal.

According to another aspect, the present disclosure provides a surgical method for a spine, a plurality of first anchor points being fixed to vertebrae at a first lateral side of the spine and a plurality of second anchor points being fixed to vertebrae at a second lateral side of the spine, the method comprising:

connecting a stabilization member of a surgical connection device to the first and second anchor points using a plurality arms, wherein the connecting locates the stabilization member:

(a) posteriorly of the anchor points at a position that is not substantially more posterior than the posterior extents of the tips of spinous processes of the vertebrae to which the anchor points are fixed; or (b) when one or more spinous processes of the vertebrae to which the anchor points are fixed have been removed, posteriorly of the anchor points at a position that is not substantially more posterior than the positions at which the posterior extents of the tips of the spinous processes of the vertebrae to which the anchor points are fixed were located prior to removal.

In one embodiment, the stabilizing member may be located substantially adjacent or level with the tips of the spinous processes. Depending on the size of the spine, the stabilization member may be positioned about 5-25 mm or about 5-35 mm or about 10-35 mm posteriorly of a plane extending through the rods or anchor points (e.g. through heads of bone screws acting as anchor points).

The plurality of arms may comprise both compression arms and traction arms as described with respect to the preceding aspect.

In the above aspects, devices and methods are described in which arms are connected either to rods attached to anchor points or to the anchor points themselves. Yet further aspects can employ a mix of these connection approaches. For example, one or more rods may be provided that are not connected to all of the relevant anchor points, and therefore one or more of the arms may be connected to rod(s) and one or more arms may be connected to anchor point(s). For example, at least one compression arm may be connected to rod(s) and at least one traction arms may be connected to anchor point(s). Anchor points to which the arms are connected directly may include only the most superior and inferior anchor points, for example. This may provide for dynamic stabilisation with increased resilient flexibility, e.g. for the purposes of motion preservation. Nevertheless, direct connection may also apply to a mid-section of anchor points or any other combination.

According to one aspect, the present disclosure provides a surgical connection device for a spine, the device comprising:

a stabilization member;

a plurality of arms to connect the stabilization member to first and second spinal rods on first and second lateral sides of a first region of the spine; and a plurality of arms to connect the stabilization member to first and second anchor points on first and second lateral sides of a second region of the spine different from the first region of the spine.

Anchor points are not to be limited to the lateral aspects of the spine. Midline anchor points as well as off axis anchor points may in be incorporated with any or all aspects of this disclosure.

In any of the aspects, where compression and traction arms are provided, one or more of the compression and traction arms may extend from the stabilization member in an anterior-lateral-superior direction and/or one or more of the compression and traction arms may extend from the stabilization member in an anterior-lateral-inferior direction.

In one embodiment:

the first compression arm extends from the stabilization member in an anterior-lateral direction towards the first rod or one of the first anchor points;

one of the first traction arms extends from the stabilization member in an anterior-lateral-superior direction from the stabilization member towards the first rod or one of the first anchor points another of the first traction arms extends from the stabilization member in an anterior-lateral-inferior direction from the stabilization member towards the first rod or one of the first anchor points;

the second compression arm extends from the stabilization member in an anterior-lateral direction towards the second rod or one of the second anchor points;

one of the second traction arms extends from the stabilization member in an anterior-lateral-superior direction from the stabilization member towards the second rod or one of the second anchor points;

another of the second traction arms extends from the stabilization member in an anterior-lateral-inferior direction from the stabilization member towards the second rod or one of the second anchor points.

In one embodiment, the stabilization member provides a single, central or off-axis posteriorly located rod with anchor points being connected solely to the stabilization member by the compression and traction arms. This embodiment may provide improved superior surgical access to the lateral nerve roots and bone allowing ease of surgical resection and bone grafting.

Connection devices disclosed herein may facilitate controlled application of forces to vertebrae for the purpose of re-alignment of the vertebrae. The forces may be transmitted to vertebrae by the anchor points, e.g., pedicle screws, optionally via rods, without pulling out the screws or breaking the pedicle. There may be provided reinforcing of the anchor point construct in all planes to resist or modulate deforming loads applied to the construct during weight bearing, e.g., prior to the fusion of the spine. The connection devices may assist in the application of forces to adjacent segments of the construct, e.g. sections defined between immediately adjacent anchor points or between a plurality of anchor points inferior to and/or superior to a section of the vertebral column that is to be fused. The connection devices may buffer against undesirable distortion at an end of the construct for example, while maintaining e.g., a lordotic or kyphotic bias, for example. Forces may be applied by the connection devices off-spinal-axis where a slight enduring scoliosis is encountered. The connection devices may provide for a triangular-cross section of reinforcement and may provide means of shaping rods and/or the vertebral column in situ as well as preventing deformation thereof due to anatomic loads and any existing deformity and scar tissue.

The stabilization member, e.g. due to its posterior location relative to the rods or anchor points, may provide a guide or reattachment surface for spinal musculature and fascia after surgery, allowing better wound closure and care. The stabilization member may allow the musculature to lie in a more anatomic post-operative plane and hence may decrease post-operative pain/stiffness. It may improve post-operative muscular power and function and provide for more efficient energy utilization of these muscles to residual un-instrumented levels. Additionally the stabilization member and/or other parts of the device, may be used as a support for further dynamic connectors between instrumented vertebrae allowing controlled yet flexible deformity correction above and below the level of fusion. Furthermore, the stabilization member and/or other parts of the device may act as a scaffold for increased bone graft attachment points and hence greater fusion mass. Still further, the stabilization member and its connected arms may act to protect the dural sac post-operatively and during any subsequent surgery, in the latter case by defining the tissue plane of the spinal canal and the contained dural sac. Furthermore, the stabilization member may act as a scaffold for an anti-adhesion polymer, (or biomer) layer, to protect the dural sac.

Surgical connection devices according to the present disclosure may comprise a support that supports the posteriorly-located stabilization member from an anterior side of the stabilization member. The support may function as a prop for the stabilization member. The support may comprise a first connector that connects between opposite lateral sides of the spine and a second connector that connects the first connector to the stabilization member.

The support may be adapted for use with a variety of different surgical connection devices. For example, in one embodiment a surgical connection device may comprise a rod that extends between opposite lateral sides of the spine and which is arced in a posterior direction. The support may provide support for the rod, e.g., at most posteriorly located portion of the rod or otherwise.

Thus, according to one aspect, there is provided a support for a surgical stabilization member, the support comprising:

a first connector adapted to connect between opposite lateral sides of the spine; and a second connector adapted to connect the first connector to the stabilization member.

The first connector may connect between first and second rods on opposite lateral sides of the spine or between first and second anchor points on opposite lateral sides of the spine. The first and second connectors may be integrated or may be separate pieces that are connected together, e.g., during surgery. The first and second connectors may each be elongate, with their directions of elongation extending substantially perpendicularly to each other. The first connector may extend in a medial-lateral direction, whereas the second connector may extend in an anterior-posterior direction. The first connector may be connected to the second connector at a centre of the second connector or otherwise. The support may be a T-shaped support. The first connector may be a cross-bar and the second connector may be a buttress.

As indicated, surgical connection devices of the present disclosure may provide stabilization while exhibiting a motion preserving function. In general, where bone fusion is carried out, articulation of the spine is substantially eliminated. The surgical connection devices may be used as an adjunct to fusion, e.g., to provide motion preserving support to vertebrae located to one or both sides of a section of fused vertebrae, or to be used in place of a spinal fusion. In either case, the surgical connection device may provide for a stabilisation region of the spine while enabling motion preservation at and/or adjacent the stabilised region.

The surgical connection device may include means for adjusting stiffness at different vertebral levels as required. The stiffness of the stabilizing member and/or the stiffness of arms connecting the stabilizing member to rods or anchor points may be adjusted depending on the degree of motion preservation required and the location of the required motion preservation. The stabilization member and/or arms may vary in stiffness through material selection, diameters and/or shape including sinuosity, e.g. flexible s-bends. The stabilization member and/or arms may have varying flexibility across different planes. For example, they may have omnidirectional flexibility, bi-directional flexibility, or uni-directional flexibility. The stabilization member and/or arms with omni-direction flexibility may have uniform flexibility in every plane or different flexibility in different planes. The stabilization member and/or arms may be straight or may be bent.

In one embodiment, arms are provided with elements such as resorbable collars that serve to stiffen the arms. The stiffening effect of the resorbable elements gradually reduces as they are resorbed over time, resulting in a progressive increasing in the flexibility of the arms.

Greater motion preservation using the connection device may be achieved through connection of the stabilization member directly to anchor points, rather than rods connected to the anchor points. For example, a first portion of the stabilization member may be connected using arms directly to first and/or second rods fixed to a first spinal portion, e.g., a fused vertebral section having three fused vertebrae or otherwise. However, another portion or portions of the stabilization member may be connected using arms directly to anchor points fixed at a second spinal portion, e.g. at non-fused section(s) of vertebrae, located superiorly and/or anteriorly to the first spinal section. In an alternative example, the stabilization member may be connected directly to anchor points only, and no first or second rods may be employed. Nevertheless, the arms connecting the stabilization member to a non-fused portion may have greater flexibility than the arms connecting the stabilization member to a fused section.

Use of stiffer arms and/or use of first or second rods at a fused portion of the spine may provide greater stability to the overall construct without providing any adverse effect to motion preservation at non-fused sections. More flexible arms connected to anchor points at non-fused sections may provide motion preserving stabilisation while decreasing the tendency for degeneration at those different vertebral levels.

In one aspect, the surgical connection device is adapted to stabilize a mobile disc replacement of a spine. The surgical connection device may provide motion preserving posterior support to the disc replacement.

In another aspect, the surgical connection device is adapted to stabilize a lateral facet joint of a spine. The surgical connection device may provide motion preserving posterior support to the lateral facet joint.

In one aspect, the present disclosure provides a surgical connection device adapted to stabilize a lateral facet joint of a spine between first and second vertebrae, comprising:

an elongate stabilization member configured to locate posteriorly of the spine such that the direction of elongation of the stabilization member is substantially parallel to the spinal axis;

at least a pair of first arms adapted to connect between the stabilization member and anchor points of the first vertebra; and at least a pair of second arms adapted to connect between the stabilization member and anchor points of the second vertebra.

In any aspects disclosed herein, the surgical connection device may control each plane of movement individually, e.g. by adjusting the stiffness and positioning of each arm to provide desired dampening of forces. The stiffness may be "tuned" to a desired level for each plane of movement. For example, the connection device may provide increased stiffness/stabilisation in one plane, e.g., a plane that prevents spondylolisthesis, while providing lower stiffness/stabilisation in other planes, e.g. planes that permit flexion and extension.

In one aspect, the present disclosure provides a surgical connection device for a spine, comprising:

an elongate stabilization member;

at least one anchor connected to a first portion of the elongate stabilization member and adapted to substantially fix the position of the stabilization member relative to the first portion of the spine, at least a first control arm connected to a second portion of the elongate stabilization member and adapted to control a movement of a second portion of the spine relative to the stabilization member.

In another aspect, the present disclosure provides a surgical method for a spine, the method comprising:

fixing the position of an elongate stabilization member relative to a first portion of a spine using at least one anchor connected between a first portion of the stabilization member and the first portion of the spine, controlling a movement of a second portion of the spine relative to the stabilization member using at least a first control arm connected between a second portion of the stabilization member and the second portion of the spine.

The anchor may connect the first stabilization member to the spine such that the stabilization member extends along the spine, e.g. in a direction substantially parallel to the spinal axis. At least the second portion of the stabilization member may locate at a position that is medial to a first lateral edge of a vertebra or vertebrae at the second portion of the spine. The first control arm may project outwardly from the second portion of the stabilization member in a direction towards the first lateral edge of the vertebra or vertebrae.

The at least one anchor may comprise one or more arms adapted to substantially fix the position of stabilization member relative to the first portion of the spine. The anchor may comprise arms as described in preceding aspects, e.g. compression arms and/or traction arms. In one embodiment, the first portion of the spine comprises fused vertebrae.

The first control arm, while connected to the second portion of the spine, controls a movement of the second portion of the spine relative to the stabilization member. In this regard, the first control arm when connected between the second portion of the stabilization member and the second portion of the spine allows relative movement between second portion of the spine and the stabilization member, in a controlled manner.

The first control arm may be rotatable relative to the second portion of the stabilization member and/or the second portion of the spine such as to control the movement of the second portion of the spine. Rotation may be achieved through the provision of an articulated joint (e.g. a hinge or pivot) between the first control arm and the second portion of the stabilization member and/or between the first control arm and the second portion of the spine.

The first control arm may be substantially rigid such as to maintain a fixed length while permitting movement between the second portion of the spine and the stabilization member. Alternatively, the first control arm may be flexible. In some instances, bending of the flexible first control arm may provide for the control of movement of the second portion of the spine in addition to or as an alternative to employing articulated joints.

In one embodiment, the surgical connection device comprises at least a second control arm in addition to the first control arm. The second control arm may be connected to the second portion of the elongate stabilization member and adapted to control movement of the second portion of the spine relative to the stabilization member.

The second control arm may be rotatable relative to the second portion of the stabilization member and/or the second portion of the spine such as to control the movement of the second portion of the spine. Rotation may be achieved through the provision of an articulated joint (e.g. a hinge or pivot) between the second control arm and the second portion of the stabilization member and/or between the second control arm and the second portion of the spine.

The second control arm may be substantially rigid such as to maintain a fixed length while permitting relative movement between the second portion of the spine and the stabilization member. Alternatively, the second control arm may be flexible. In some instances, bending of the flexible second control arm may provide for the control of movement of the second portion of the spine in addition to or as an alternative to employing articulated joints.

Thus, the second control arm may be configured similarly to the first control arm. However, the second control arm may be project from the stabilization member in a substantially opposite direction from the first control arm.

As discussed above, the second portion of the stabilization member may locate at a position that is medial to a first lateral edge of a vertebra or vertebrae at the second portion of the spine. Additionally, the second portion of the stabilization member may locate at a position that is medial to a second lateral edge of the vertebra or vertebrae at the second portion of the spine, the second lateral edge being opposite to the first lateral edge. Thus, the second portion of the stabilization member may locate centrally between first and second opposite lateral edges of the spine. The first control arm may project outwardly from the second portion of the stabilization member in a direction towards the first lateral edge and the second control arm may project outwardly from the second portion of the stabilization member in a direction towards the second lateral edge.

One of the first and second control arms may project in a superior-lateral direction from the second portion of the stabilization member and the other of the first and second control arms may projection in an inferior-lateral direction from the second portion of the stabilization member.

The second portion of the spine may comprise a single vertebra or multiple vertebrae, which vertebra or vertebrae may be located at a different position along the spine from the first portion of the spine. The first and control arms may connect to the same vertebra or to different vertebrae.

The connection device may be used in conjunction with one or more rods and/or anchor points. For example, a plurality of first anchor points may be fixed to vertebrae of the spine at a first lateral side of the spine, a plurality of second anchor points being fixed to vertebrae at a second lateral side of the spine. A first spinal rod may be attached to the plurality of first anchor points and/or a second spinal rod may be attached to the plurality of second anchor points. The anchor and/or control arms may be connected to the spine through connecting to the first and second anchor points and/or first and second rods. In some embodiments, the stabilization member may extend over the entire length of instrumentation secured to the spine. While there may be sections of the spine which include e.g. first and/or second rods as described above, the stabilization member may be the primary guiding element for derogation and straightening of the vertebral column.

By providing at least a first control arm, or at least first and second control arms, which arm(s) control movement of the second portion of the spine relative to the stabilization member, the surgical connection device may provide for re-alignment of the spine. Where a recipient of the surgical connection device is a child, for example, general movement of the second portion of the spine may occur as a result of growth of the spine post-implantation. The growth may be such as to move the second portion of the spine in a direction away from the first portion of the spine. However, by connecting the first control arm to the second portion of the spine, the direction of growth at the second portion of the spine may be controlled by the surgical connection device. For example, the control arm(s) may each be movable in a respective single plane. Relative lengthening of the spinal column may force the arms to rotate through an arc in the respective plane. The orientation of each plane can be selected to drive a desired correction of the tilt and rotation of the spine. Assisting in this process is the anchoring of the stabilization member to a different, first portion of the spine. In some embodiments, the stabilization member may be anchored to multiple portions of the spine, e.g. different sections of fused vertebrae, providing for intermittent anchoring of the stabilization member along the surgical connection device. In some embodiments, the intermittently anchored portions of the stabilization member may be interleaved with portions of the stabilization member that are rotatably connected to the spine. In general, the connection device may anchor/fix at one or more vertebral levels and provide for controlled rotation movement at one or more other vertebral levels.

The surgical connection device, while not restricting growth of the spine, may therefore force a straightening or other type of shape adjustment of the spine during growth of the spine. This may be particularly advantageous to treat scoliosis of the spine in children, although the connection device is not necessarily limited to such use. By taking the approach disclosed, growth of the spinal column may not be retarded, the need for re-operation to allow growth may be obviated or at least reduced, and correction of the spine can be achieved post-operatively and in a gradual fashion.

According to the present disclosure, one or more of the above aspects may be combined with one or more of the other above aspects. Furthermore, any of the above aspects or combination of aspects may be combined with any of the optional features discussed herein.

BRIEF DESCRIPTION OF DRAWINGS

Embodiments of the present disclosure are now described by way of example only with reference to the accompanying drawings, in which:

FIG. 4b shows a transverse view of the connection arrangement of FIG. 4a;

DESCRIPTION OF EMBODIMENTS

Embodiments of the present disclosure relate to posterior spinal surgery, including spinal fixation surgery, used in the treatment of spinal conditions such as spondylolisthesis, scoliosis, spinal trauma, spinal tumor and other spinal deformities or degenerative conditions. The surgery can involve inserting pedicle screws into vertebrae to establish anchor points. A stabilizing rod can then be secured between several of the anchor points to restrict or limit relative movement between vertebrae. This process can be carried out on opposite sides of the spine such that first and second rods are in place. When the posterior spinal surgery is completed, spinal fusion may be carried out through bone grafting and other means.

Embodiments of the present disclosure also relate to motion preservation devices, e.g. for use in conjunction with a mobile disc replacement or otherwise. In general, where bone fusion is carried out, articulation of the spine is substantially eliminated. Surgical connection devices according to embodiments of the present disclosure may be used as an adjunct to fusion, e.g., to provide motion preserving support to vertebrae located to one or both sides of a section of fused vertebrae, or to be used in place of a spinal fusion. In either case, the surgical connection device may provide for a stabilisation region of the spine while enabling motion preservation at or adjacent the stabilised region.

Figure 1A:
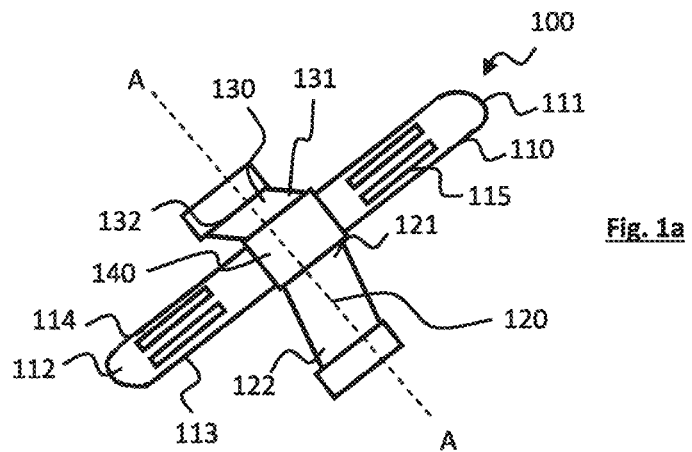
FIG. 1a shows a perspective view of a surgical connection device according to an embodiment of the present disclosure.
Figure 1B:
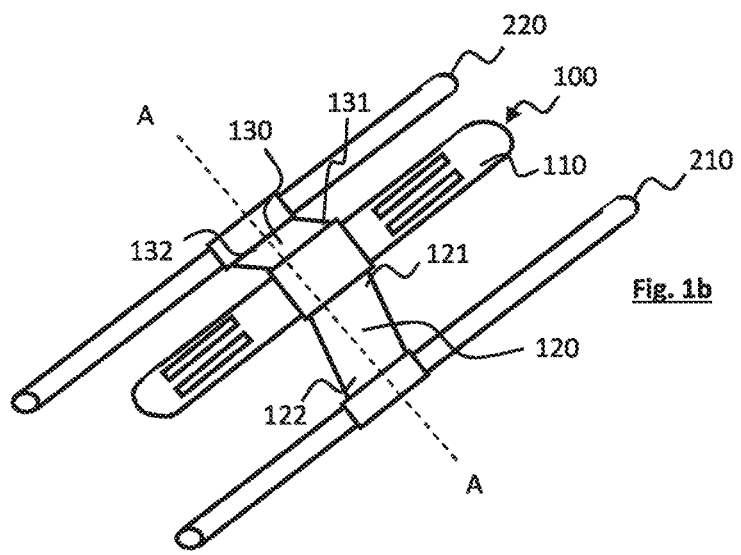
FIG. 1b shows a perspective view of the surgical connection device of FIG. 1a connected to first and second rods.
Figure 1C:
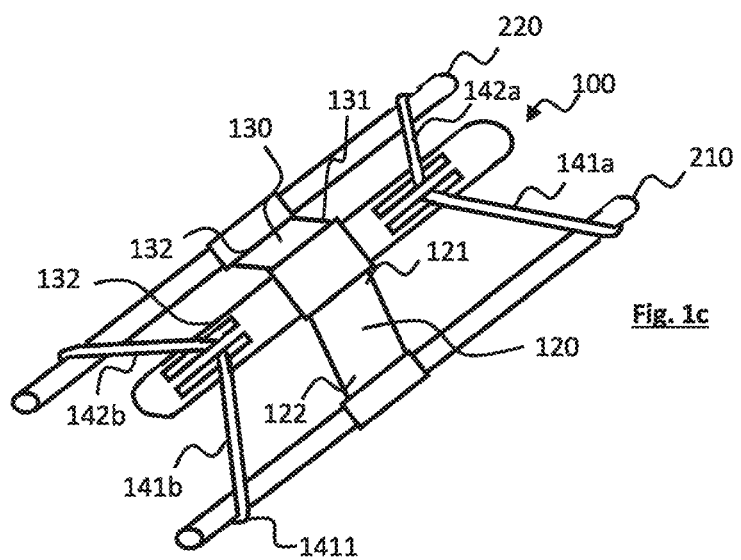
FIG. 1c shows a perspective view of the surgical connection device of FIG. 1b with traction arms.
Figure 2A:
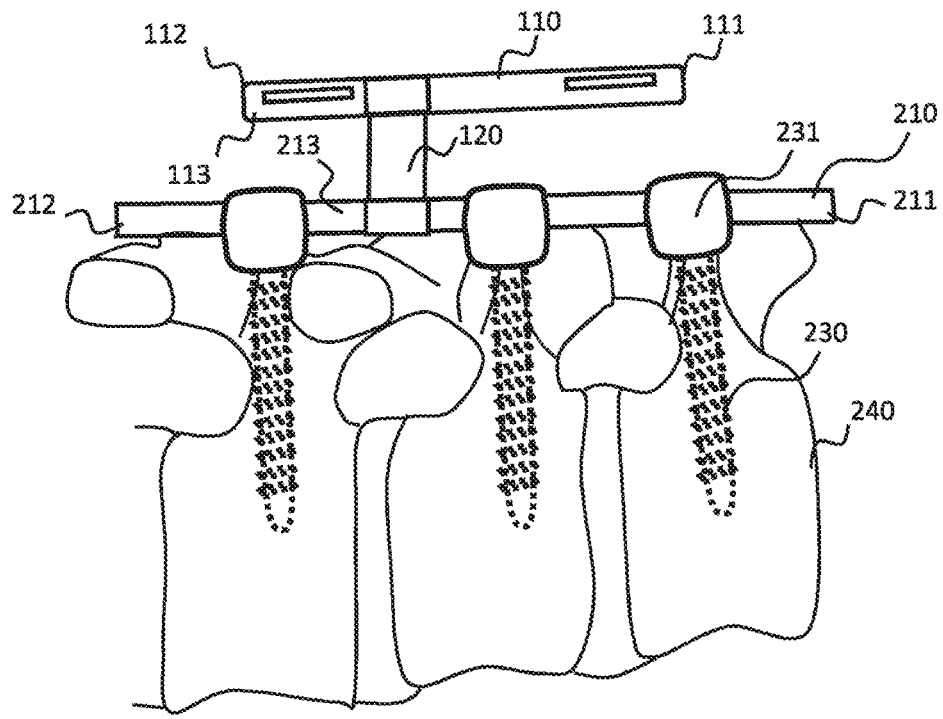
FIG. 2a shows a lateral view of the surgical connection device of FIG. 1b connected to first and second rods, the rods being anchored to vertebrae via pedicle screws.

Perspective views of a surgical connection device 100 according to an embodiment of the present disclosure are provided in FIGS. 1a to 1c. The connection device 100 includes an elongate stabilization member 110 including a superior end 111 and an inferior end 112 and walls extending between the superior end 111 and the inferior end 112, including a first wall 113 and second wall 114. First and second compression arms 120, 130 extend on substantially opposite sides of the stabilization member 110 to connect the stabilization member 110 to first and second rods 210, 220, generally as represented in FIG. 1b. With reference also to FIG. 2a (which shows the first rod 210 only), the first and second rods 210, 220 are fixed to anchor points, in particular to heads 231 of pedicle screws 230, implanted in vertebrae 240.

The connection device 100 has a cruciform structure, with the axis of elongation of the stabilization member 110 configured to lie substantially parallel to the spinal axis and to the axes of elongation of the first and second rods 210, 220 when implanted.

Referring to FIG. 1b, the first compression arm 120 has a first end 121 that is connected to the stabilization member 110 and a second end 122 that is connected to the first rod 210. Similarly, the second compression arm 130 has a first end 131 that is connected to the stabilization member 110 and a second end 132 that is connected to the second rod 220. In this embodiment, the first ends 121, 131 of the compression arms 120, 130 are permanently fixed to the stabilization member 110 (e.g. through integral forming or otherwise). In alternative embodiments, the connection arms 120, 130 may be connected to the stabilization member 110 during use, e.g. by a surgeon.

The first and second compression arms 120, 130 each extend both anteriorly and laterally from the stabilization member 110. Thus, when connected to the first and second rods 210, 220, the stabilization member 110 locates posteriorly and medially of each of the first and second rods 210, 220. A cross-sectional view of the device 100 along line A-A of FIG. 1b. i.e. in a transverse plane of the device 100 extending through the first and second compression arms 120, 130, is provided in FIG. 3a. The cross-section can be considered substantially v-shaped or u-shaped.

Figure 2B:
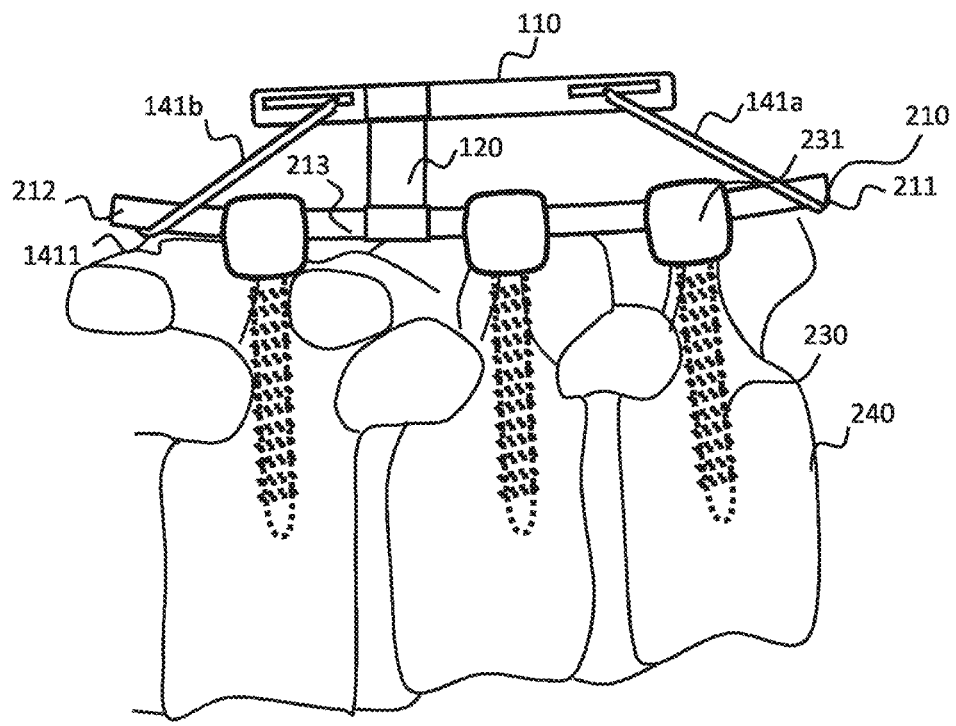
FIG. 2b shows a lateral view of the surgical connection device of FIG. 1c connected to first and second rods, the rods being anchored to vertebrae via pedicle screws.

Referring to FIGS. 1c and 2b, after the compression arms 120, 130 are connected to the first and second rods 210, 220, two pairs of traction arms are connected between the stabilization member 110 and the rods 210, 220. In particular, a pair of first traction arms 141a, 141b is connected between the stabilization member 110 and the first rod 210 and a pair of second traction arms 142a, 142b is connected between the stabilization member and the second rod 220. Each of the traction arms has a first end connected to the stabilization member 110 and a second end connected to the respective rod 210, 220. In an alternative embodiment, adjacent traction arms, e.g. a first traction arm 141a and a second traction arm 142a, or a first traction arm 141b and a second traction arm 142b, may be joined to form a v-shaped or u-shaped element, with the apex of the v- or u-shape being secured to the stabilization member 110.

The pair of first traction arms 141a, 141b are connected to the first rod 210 at positions on either side of the position at which the first compression arm 120 is connected to the first rod 210. In particular, one of the first traction arms 141a is connected to the first rod 210 at a position that is superior to the position at which the first compression arm 120 connects to the first rod 210 and the other first traction arm 141b is connected to the first rod 210 at a position that is inferior to the position at which the first compression arm 120 connects to the first rod 210. Similarly, the pair of second traction arms 142a, 142b are connected to the second rod 220 at positions on either side of the position at which the second compression arm 130 connects to the second rod 220. In particular, one of the second traction arms 142a is connected to the second rod 220 at a position that is superior to the position at which the second compression arm 130 is connected to the second rod 220 and the other second traction arm 142b is connected to the second rod 220 at a position that is inferior to the position at which the second compression arm 130 connects to the second rod 220.

The traction arms 141a, 141b. 142a, 142b are connected to the stabilization member 110 via slots 115 provided in the stabilization member 110. In this embodiment, the traction arms 141a, 141b, 142a, 142b generally have a fixed angle to the rods 210, 220 and can be slid along a respective one of the slots 115 to be connected to the stabilization member 110 at an appropriate location.

When the device 100 is implanted, the first compression arm 141a extends from the stabilization member 110 in an anterior-lateral (right) direction towards the first rod 210, the second compression arm extends from the stabilization member 110 in an anterior-lateral (left) direction towards the second rod 220; one of the pair of first traction arms 141a extends from the stabilization member 110 in an anterior-lateral (right)-superior direction towards the first rod 210, the other one of the pair of first traction arms 141b extends from the stabilization member 110 in an anterior-lateral (right)-inferior direction towards the first rod 210, one of the pair of second traction arms 142a extends from the stabilization member 110 in an anterior-lateral (left)-superior direction towards the second rod 220, and the other one of the pair of second traction arms 142b extends from the stabilization member 110 in an anterior-lateral (left)-inferior direction towards the second rod 220.

The two pairs of traction arms 141a. 141b, 142a, 142b are placed under tension between the stabilization member 110 and the first and second rods 210, 220, resulting in superior and inferior portions of each of the first and second rods 210, 220 being pulled towards the stabilization member 110 while the first and second compression members 120, 130 maintain an intermediate portion of each of the first and second rods 210, 220, located between the superior and inferior portions, at a substantially fixed distance away from the stabilization member 110. The controlled application of tensile forces and compressive forces to different portions of the first and second rods 210, 220 can straighten the first and second rods 201, 220, change a direction of bending of the first and second rods 210, 220 or increase a degree of bending of the first and second rods 210, 220. Bending of the first rod 210, following connection of the traction arms 141a, 141b, 142a, 142b, is illustrated in FIG. 2b. As can be seen, superior and inferior portions 211, 212 of the first rod 210 have been bent posteriorly, in comparison to their positions as shown in FIG. 2a, whereas an intermediate portion 213 of the first rod has remained in a substantially fixed position. In this example, the rod 210 has been drawn into lordosis or further lordosis. Where a kyphotic deformity or correction is desired the positions of the compression and traction arms may be reversed. Compression arms may be located to outer sides of the stabilization device and traction arms may take the intermediate position.

Figure 6:
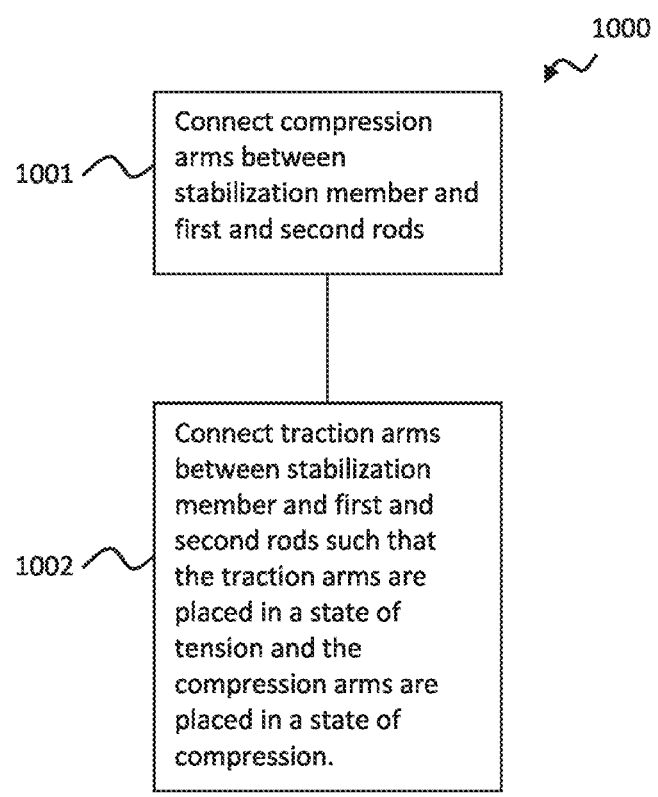
FIG. 6 shows a flow chart indicating steps carried out to connect the connection device to first and second rods according to an embodiment of the present disclosure.

A flow chart 1000 indicating steps carried out to connect the connection device 100 to the first and second rods is provided in FIG. 6. At step 1001, compression arms are connected between the stabilization member and the first and second rods. At step 1002, traction arms are connected between stabilization member and first and second rods such that the traction arms are placed in a state of tension and the compression arms are placed in a state of compression.

Figure 3A:
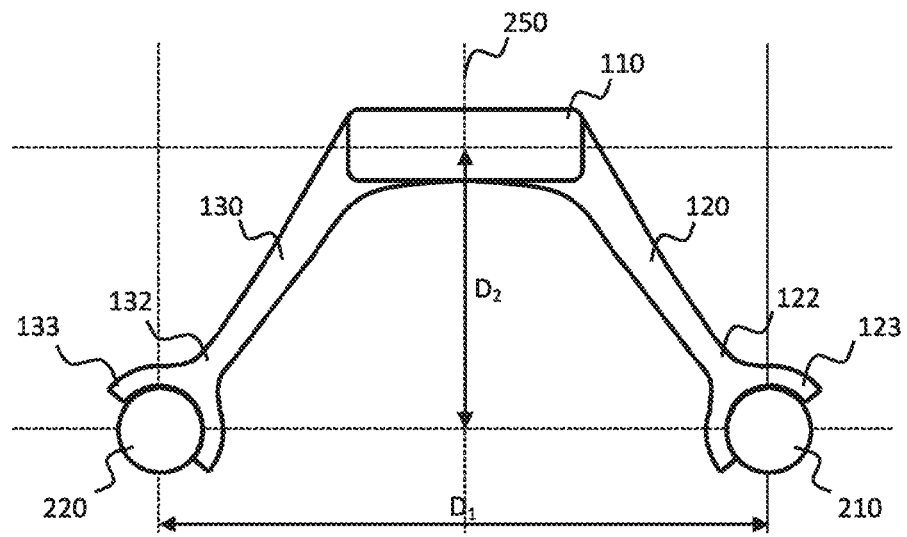
FIG. 3a shows a cross-sectional view of the surgical connection device along line A-A of FIG. 1b.

The device 100 can be manufactured in a variety of different shapes and sizes, e.g., for use with spines of differing sizes or for use at spinal portions that have or have not been subjected to a laminectomy. Referring to FIG. 3a, the distance Di by which second ends 122, 132 of the compression arms 120, 130 are separated in a transverse direction can be modified to enable use of the device 100 with differently-spaced first and second rods 210, 220. Further, the distance $D_2$ by which the stabilization member 110 is set back posteriorly from the first and second rods 210, 220 can be modified in accordance with the size or configuration of the spine. The distances Di, $D_2$, may be modified during manufacture of the device 100 and/or may be adjustable during use of the device, e.g. through manual bending of the compression arms 120, 130 or otherwise. In general, depending on the size of the spine, the device may be configured such that the stabilization member is positioned about 5-25 mm or 5-35 mm or 10-35 mm posteriorly of a plane extending through the rods or otherwise.

The stabilization member may therefore provide a third elongate stiffening element, e.g. a form of third rod, which is posteriorly located relative to the first and second rods. By positioning the stabilization member posteriorly of the first and second rods, and through the provision of both traction and compression arms, a surgeon may be provided with a significantly increased ability to control the application of forces applied to vertebrae via the first and second rods for the purpose of re-alignment and/or stabilization of the vertebrae. Substantial forces may be applied to the rods via the arms in any direction in three-dimensional space. The forces may be transmitted to vertebrae by pedicle screws attached to the rods, without pulling out the screws or breaking the pedicle. There may be provided reinforcing of the rod/screw construct in all planes to resist or modulate deforming loads applied to the construct during weight bearing, e.g., prior to the fusion of the spine. The devices and apparatus may assist in the application of forces to adjacent segments of the rod/screw construct, e.g. sections defined between immediately adjacent pedicle screws or between a plurality of pedicle screws. The devices and apparatus may buffer against undesirable distortion at an end of the construct for example, while maintaining e.g., a lordotic or kyphotic bias, for example. These forces may be applied off-spinal-axis where a slight enduring scoliosis is encountered. The devices and apparatus may provide for a triangular-cross section of reinforcement and may provide means of shaping rods in situ.

Figure 3B:
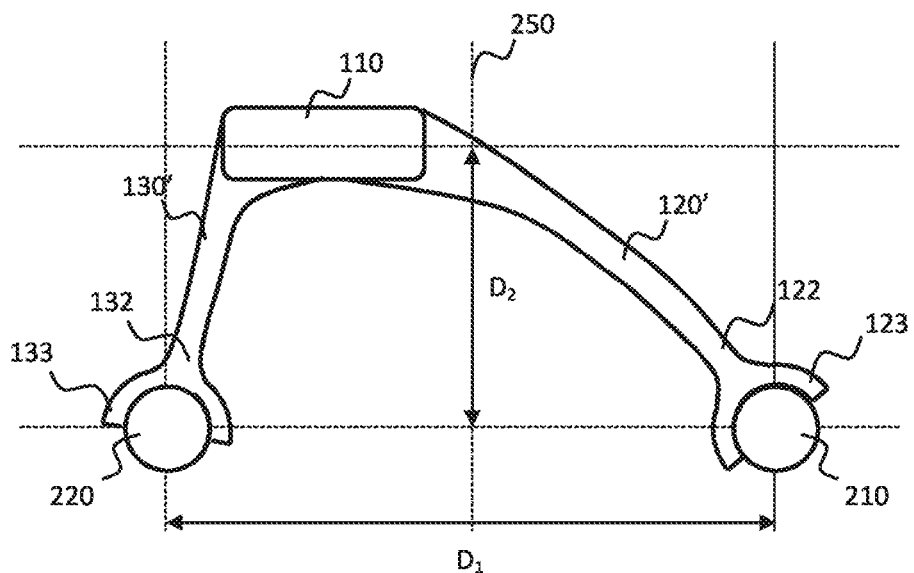
FIG. 3b shows a cross-sectional view of a surgical connection device according to an alternative embodiment of the present disclosure.

While the device 100, e.g., as illustrated in FIG. 3*a*, is arranged to be substantially symmetrical about the mid-sagittal plane 250, in alternative embodiments the device 100 may be asymmetrically arranged about the mid-sagittal plane 250. For example, as shown in FIG. 3*b*, the stabilization member 110 may be positioned laterally of the mid-sagittal plane 250. To achieve this, one of first and second compression arms 120', 130' may be longer than the other of the first and second compression arms 120', 130'. This off-axis or eccentric positioning of the stabilization member 110 can enable the stabilization member 110 to locate laterally of the tips of the spinous processes, making the device more suitable for positioning over vertebrae that have not been subjected to a laminectomy. It can also enable the device to handle application of more complex forces, e.g. associated with scoliotic spines, or in children with growing spines.

Figure 8:
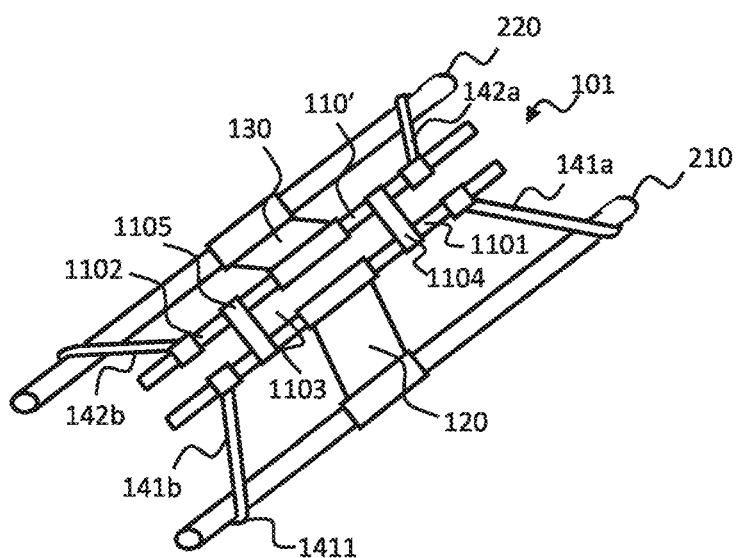
FIG. 8 shows a perspective view of the surgical connection device of FIG. 1c with a modified stabilization member.

In an alternative embodiment, to enable the connection device to be used in conjunction with vertebrae that have not been subjected to a laminectomy, while positioning the stabilization member on the mid-sagittal plane, the stabilization member may comprise a central opening to receive one or more spinous processes. For example, with reference to FIG. 8, a connection device 101 according to an embodiment of the present disclosure may be configured substantially in accordance with the connection device 100 described with respect to preceding embodiments, but the stabilization member 110' may comprise first and second stabilizing rods 1101, 1102 that each extend along the spine and which are spaced apart in a medial-lateral direction such as to provide a gap 1103 to accommodate tips of the spinous processes. Connectors 1104, 1105 connect the two stabilizing rods 1101, 1102 together. The connectors are configured to extend through interspinous spaces between adjacent spinous processes, without obstruction to the spinous processes. In alternative embodiments, connectors 1104, 1105 may additionally or alternatively extend through an interspinous ligament and/or through a spinous process or any other structure located between the stabilizing rods 1101, 1102.

Referring again to FIGS. 1*a* to 1*c*, while the first ends 121, 131 of the compression arms 120, 130 in the device 100 are fixed in position relative to the stabilization member 110, in alternative embodiments the connection positions of the first ends of the compression arms may be adjustable relative to the stabilization member. For example, the first ends of the compression arms may be fixed to the stabilization member via a sleeve that is slidable along the stabilization member. By sliding the sleeve along the stabilization member, the positions at which the first and second compression arms extend from the stabilization member can be adjusted along the spinal axis, enabling the compression arms to better position between anatomical features, and/or force to be applied via the compression arms at more desirable positions of the rods. When desired positions are achieved, the sleeve can be fixed to the stabilization member, e.g., using a locking screw.

The second ends 122, 132 of the compression arms 120, 130 may be connected to the respective rods 210, 220 via a connection element such as an integral or separately formed sleeve or foot-piece, which is clamped to the rod 210, 220. If the rods 210, 220 are not parallel, as is often the case, the compression arms 120, 130 may be bent manually to accommodate this non-parallel rod alignment without weakening their resistance to compression. Example foot-pieces 123, 133, which mount to the rods 210, 220, are illustrated in FIGS. 3*a* and 3*b* for example, which foot pieces 123, 133 each have an engagement surface that contacts a posterior surface of the rod around approximately 180 degrees of the rod circumference.

Figure 4A:
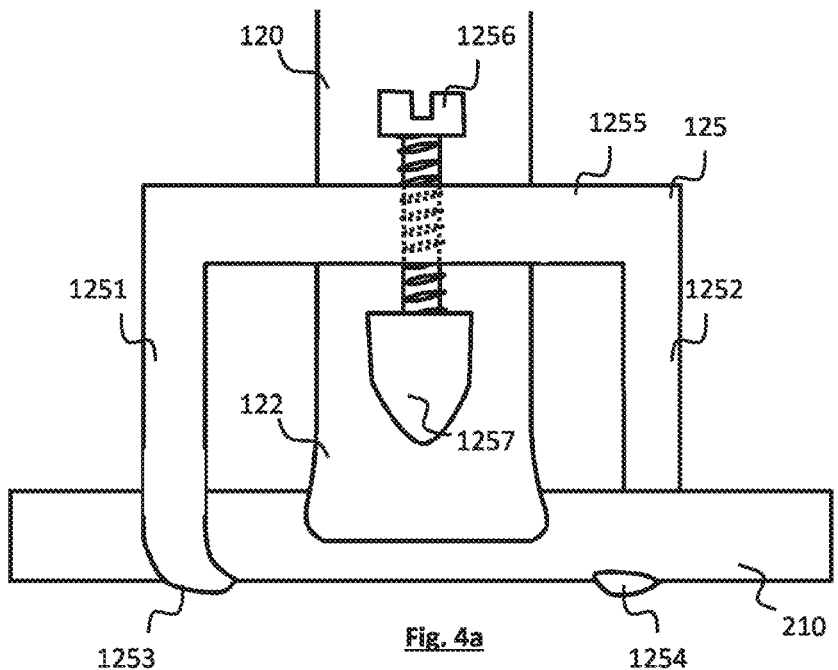
FIG. 4a shows a lateral view of a connection arrangement for connecting a compression arm of a surgical connection device according to an embodiment of the present disclosure to a rod.
Figure 4B:
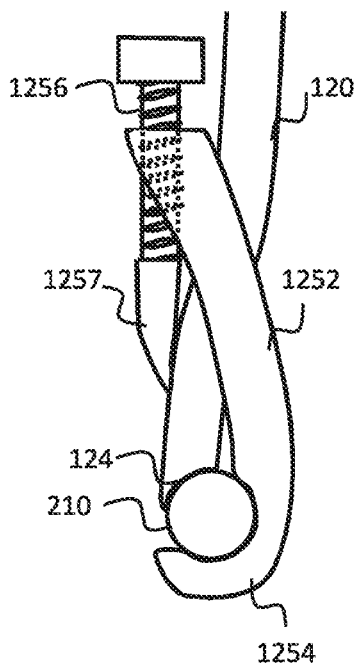

To provide for increasingly secure engagement between the compression arms 120, 130 and the rods 210, 220, a connection arrangement may be provided as illustrated in FIGS. 4*a* and 4*b*, for example. At the second end 122 of the compression arm 120, the compression arm 120 has a curved abutment surface 124 for engaging a posterior surface of the rod 210. A lock unit 125 is provided, including a pair of capture legs 1251, 1252 having hooked distal ends 1253, 1254, the capture legs 1251, 1252 depending from opposite sides of a cross beam 1255. The hooked distal ends 1253, 1254 hook onto anterior surfaces of the rod 120 on either side of the compression arm 120, via medial and lateral sides, respectively, of the rod 210. The curved abutment surface 124 of the compression arm 120 and the hooked distal ends 1253, 1254 of the capture legs 1251, 1252 are drawn towards each other, such as to clamp to either side of the rod 210, through tightening of a locking screw 1256 that extends through the cross beam 1245 of the locking unit 124 and which has an abutment 1257 that presses the second end 122 of the compression arm 120 towards the rod 210.

The second ends of the traction arms 141*a*, 141*b*, 142*a*, 142*b* may be connected to the respective rods 210, 220 via hook elements 1411, as indicated very generally in FIGS. 1*c* and 2*b*, which hook elements 1411 hook underneath anterior surfaces of the rods 210, 220.

Figure 5A:
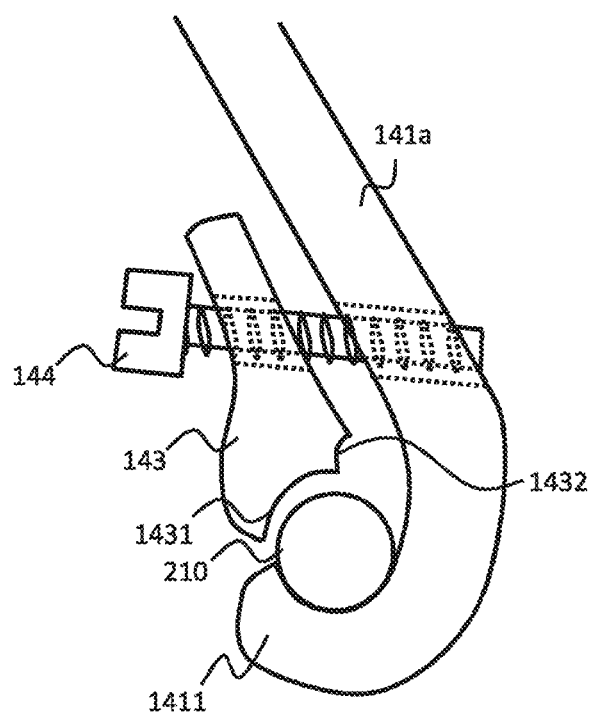
FIG. 5a shows a transverse view of a connection arrangement for connecting a traction arm of a surgical connection device according to an embodiment of the present disclosure to a rod.
Figure 5B:
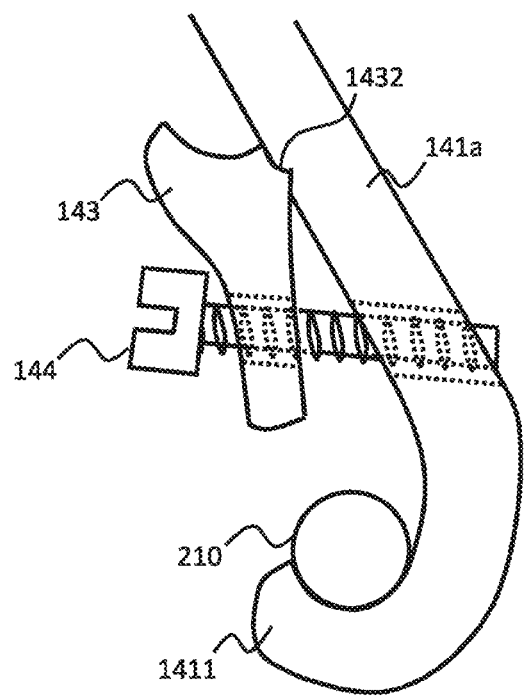
FIG. 5b shows a transverse view of the connection arrangement of FIG. 5a with a locking piece thereof moved vertically.

To provide for increasingly secure engagement between the traction arms 141*a*, 141*b*, 142*a*, 142*b* and the rods 210, 220, a locking piece 143 can be provided as illustrated in FIGS. 5*a* and 5*b*, for example. The locking piece 143 has a curved abutment surface 1431 that is forced down on a posterior surface of the respective rod 210 such that the rod is clamped between the locking piece 143 and the hook element 1411. The locking piece 143 is secured to the traction arm 141*a* via a screw 144 that extends both through the locking piece 143 and the traction arm 141*a*, and which screw 141*a* can be tightened to increase the clamping force.

The screw 144 also provides a pivot for the locking piece 143, around which the locking piece 143 can rotate relative to the traction arm 141*a*. When the screw 144 is in a loosened stated, the locking piece 143 can pivot away from the hook element 1411 to a storage position as illustrated in FIG. 5*b*, providing a clear access path for the rod 210 to move towards and engage the hook element 141. The locking piece 144 includes a recessed section 1432 to snap-fit with the traction arm 141*a* when in the storage position, maintain the locking piece 143 in the storage position prior to clamping.

In connection devices according to embodiments of the present disclosure, the stabilization member can have the added benefit of providing a guiding or reattachment surface for spinal musculature and fascia after surgery, allowing better wound closure and care. It may allow the musculature to lie in a more anatomic post-operative plane and hence may decrease post-operative pain/stiffness. It may improve post-operative muscular power and function and provide for more efficient energy utilization of these muscles to residual un-instrumented levels. Additionally, the stabilization member and/or other parts of the device, may be used as a support for further dynamic connectors between instrumented vertebrae allowing controlled yet flexible deformity correction superior to and/or inferior to the fused section. Furthermore, the device may act as a scaffold for increased bone graft attachment points and hence greater fusion mass.

Figure 7:
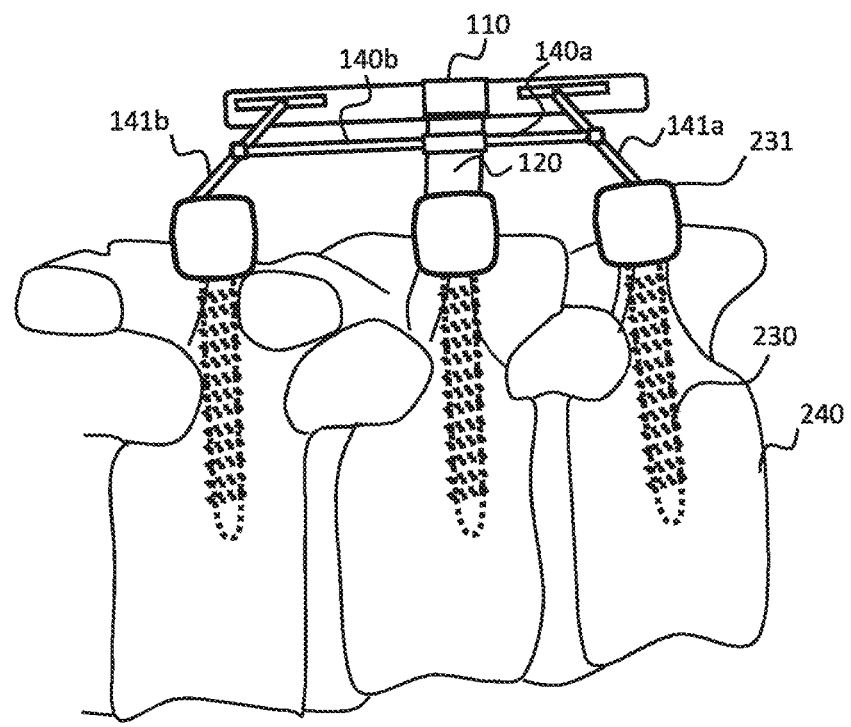
FIG. 7 shows a lateral view of a surgical connection device according to another embodiment of the present disclosure connected to pedicle screws.

In a further embodiment of the present disclosure, as illustrated in FIG. 7, the connection device 100 is adapted for use with a spine that has no first and second rods 210, 220 attached to pedicle screws 230. In this instance, the compression and traction arms 120, 130, 141a, 141b, 142a, 142b are connected directly to the heads 231 of the pedicle screws 230. Transverse or longitudinal stiffening members 140a, 140b are optionally provided between the traction and compression arms, in a variety of arrangements, to create a stiffer construct for stabilising the spine to lead to fusion.

In a further variation, a combination of traction and compression arms may be employed with or without further stiffening additions, to retain a kyphotic, lordotic and rotational stiffness, yet allow longitudinal displacement of the pedicle screws (or other vertebral securing means) with respect to each other, as is desirable to occur with growing, younger scoliotic patients. By this expedient approach, repeated surgeries or stunting of growth may be obviated while still correcting the deformity of scoliosis in younger patients. The longitudinal "play" in the arms can be achieved by uniaxial pliability in their formed shape, such as can be generated by a single plane of spring forming within the material and stiffening cross members for rotational stability.

Figure 9:
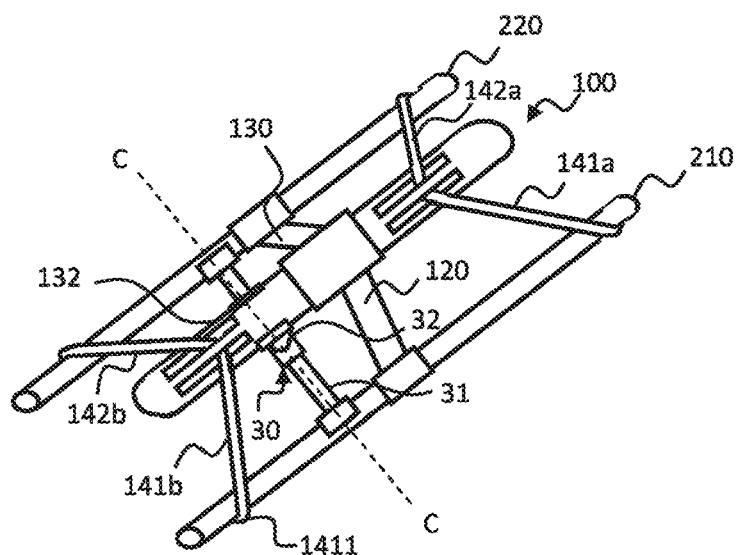
FIG. 9 shows a perspective view of the surgical connection device of FIG. 1c with an additional support
Figure 10:
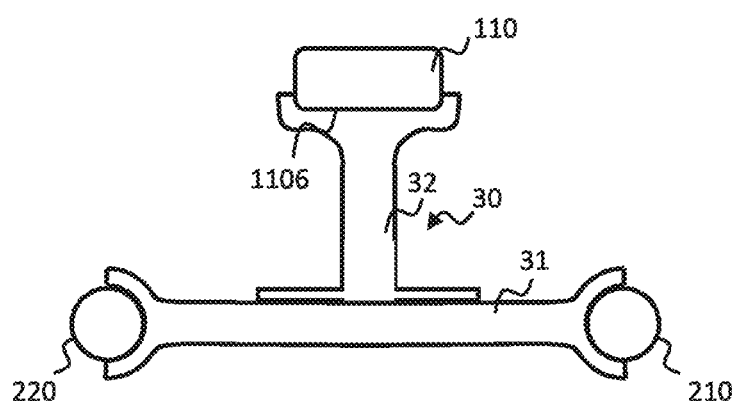
FIG. 10 shows a cross-sectional view of the surgical connection device of FIG. 9 along line C-C of FIG. 9.

With reference to FIGS. 9 and 10, in one embodiment of the present disclosure the surgical connection device 100 further comprises a support 30 for supporting the stabilization member 110 from an anterior side. The support 30 functions as a prop for the stabilization member 110, helping maintain the stabilization member 110 in a posteriorly located position. The support 30 has first connector, in particular a cross-bar 31 that connects between the first and second rods 210, 220 on opposite lateral sides of the spine, and a second connector, in particular a buttress 32 that connects between the cross-bar 31 and an anterior surface 1106 of the stabilization member 110.

The cross-bar 31 and buttress 32 can be integrally formed or can be separate pieces that are assembled during surgery, e.g. by being snap-fit to each other and/or to the stabilization member 110 and first and second rods 210, 220. The cross-bar 31 and buttress 32 are each elongate, with their directions of elongation extending substantially perpendicularly to each other. The cross-bar 31 extends in a medial-lateral direction and the buttress 32 extends in an anterior-posterior direction, providing in combination a generally T-shaped support 30.

Figure 11:
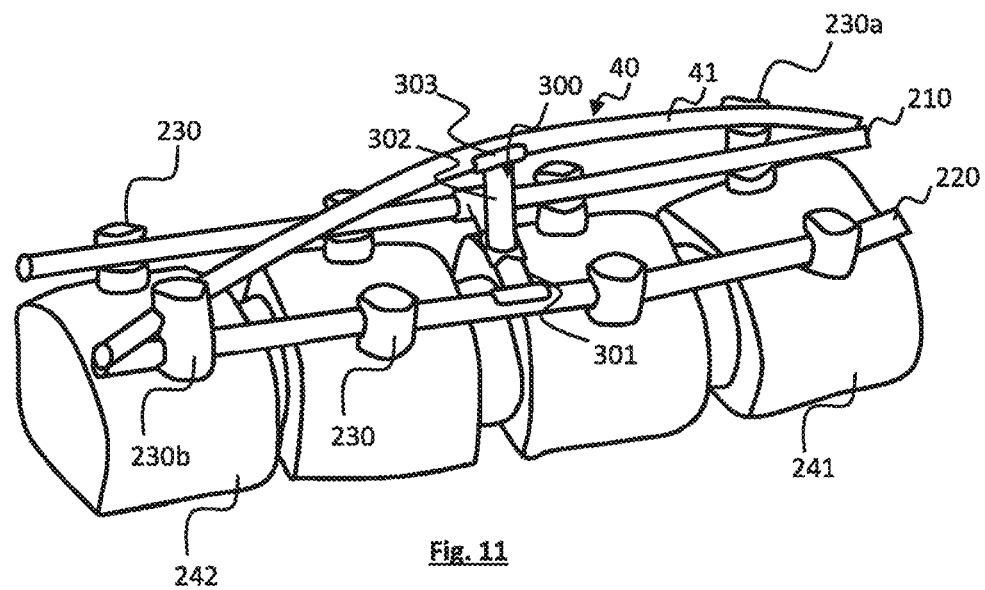
FIG. 11 shows a perspective view of a surgical connection device according to another embodiment of the present disclosure.

A support configured in a similar manner to the support 30 described above can be used in conjunction with other types of surgical connection devices according to embodiments of the present disclosure. In one embodiment, with reference to FIG. 11, a surgical connection device 40 is used to provide stabilization at a section of the spine where first and second rods 210, 220 are again connected to a plurality of first and second anchor points 230. The connection device 40 includes an arched rod 41 connected diagonally between a first anchor point 230a implanted in a first vertebra 241 and a second anchor point 230b implanted in a second vertebra 242, the first and second anchor points 230a, 230b being positioned substantially on opposite lateral sides of the spine. A support 300 is provided that again has a cross-bar 301 that connects between the first and second rods 210, 220 on opposite lateral sides of the spine and a buttress 302 that connects between the cross-bar 31 and an anterior surface of the arched rod 41 such as to maintain the curvature of the arched rod 41 and/or provide an increased tension in the arched rod 41. The buttress 302 includes a contact piece 303 to connect to the arched rod 41. The arched rod 41 may induce asymmetric corrective movement in the spine or otherwise.

Figure 12:
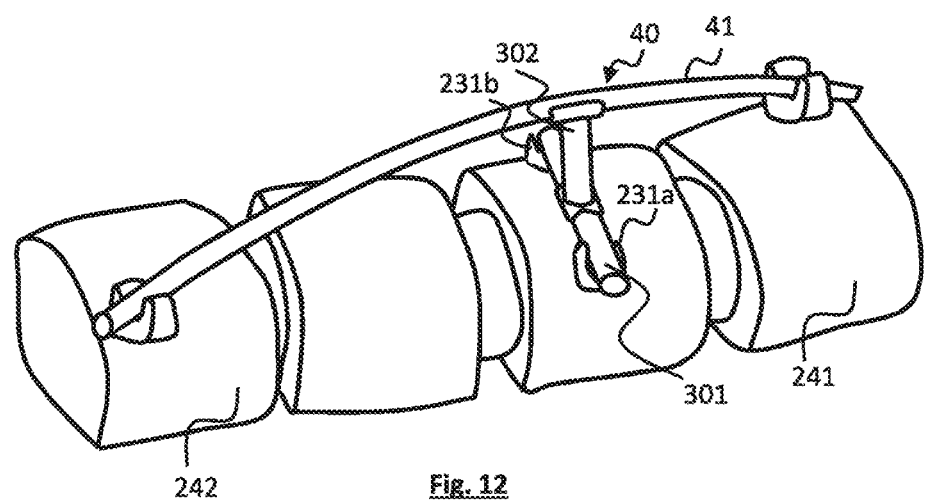
FIG. 12 shows a perspective view of a surgical connection device according to yet another embodiment of the present disclosure.

With reference to FIG. 12, in another embodiment, the arched rod 41 is used to stabilize a spinal section that has no first and second rods connected on opposite lateral sides of the spine. In this embodiment, the cross-bar 301 of the support 300 is connected directly between anchor points 231a, 231b, rather than rods.

Figure 13:
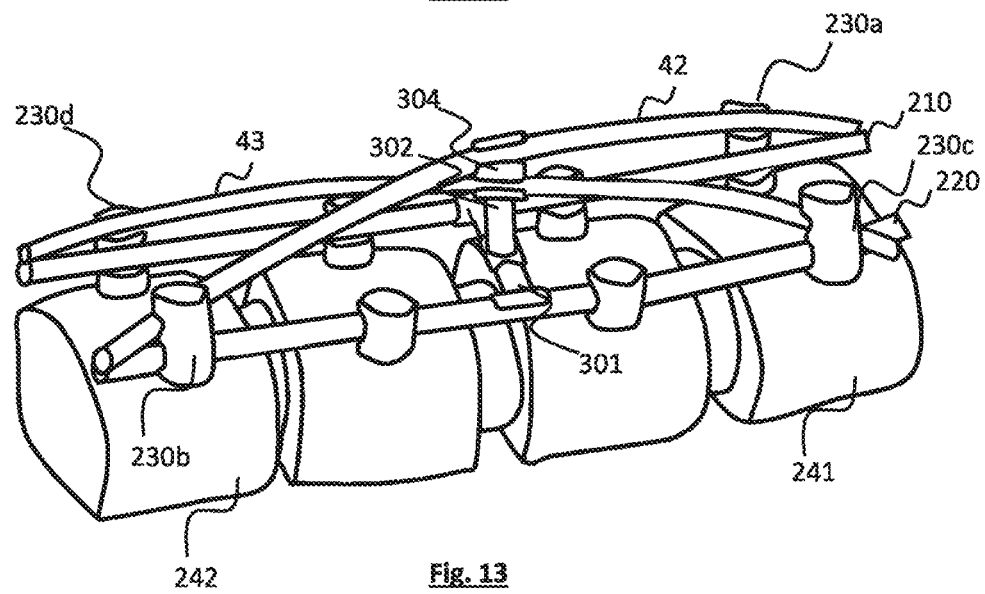
FIG. 13 shows a perspective view of a surgical connection device according to another embodiment of the present disclosure.

With reference to FIG. 13, in yet another embodiment, two arched rods are provided, including a first arched rod 42 and second arched rod 43. The first arched rod 42 is connected diagonally between a first anchor point 230a implanted in a first vertebra 241 and a second anchor point 230b implanted in a second vertebra 242. The second arched rod 43 is connected diagonally between a third anchor point 230c implanted in the first vertebra 241 and a fourth anchor point 230d implanted in the second vertebra 242. The first and fourth anchor points 230a, 230d are positioned on substantially opposite lateral sides of the spine to the second and third anchor points 230b, 230d. The first and second arched rods 42, 43 cross each other. Substantially at the position at which the first and second arched rods 42, 43 cross each other, the support 300 is provided, the support including a cross-bar 301 and a buttress 302 substantially as described above with reference to FIG. 11, but with a modified contact piece 304 to enable the buttress to connect to anterior surfaces of both arched rods 42, 43. The support 300 may maintain curvature of the two arched rods 42, 43 and/or provide increased tension in the arched rods 42, 43. The arched rod 42, 43 may induce asymmetric or symmetric corrective movement in the spine, depending on whether or not different tensile forces are applied across each rod 42, 43.

Diagonally extending arched rods 41, 42, 43, connected to substantially straight first and second rods 210, 220, are described above with reference to FIGS. 11 to 13. However, in alternative embodiments, diagonally extending rods that are substantially straight may be provided, which are optionally connected to arched first and second rods. In general, the diagonally extending rods may have a variety of different shapes. They may be in the form of a spring, e.g., a helical spring, or they may have sinuosity such as an s-shape.

In any of the embodiments disclosed herein, the surgical connection device may modify the stiffness of the spine at different positions of the spine, e.g. at different vertebral levels, to different degrees. The stiffness may be may be modified through the provision of a stabilizing member with varying stiffness over its length, and/or through the provision of arms connecting the stabilizing member to rods or anchor points that have differing stiffness properties. The stiffness may be selected depending on the degree of motion preservation required and the location of the required motion preservation. The stabilization member and/or arms may vary in stiffness through material selection, diameters and/or shape including sinuosity, e.g. flexible s-bends.

Figures 14A, 14B:
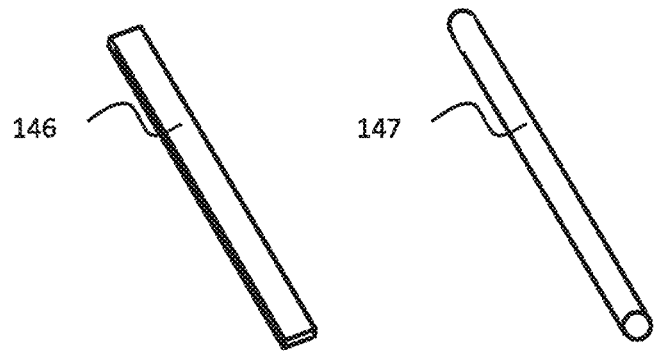
FIGS. 14a and 14b show perspective view of arms usable in surgical connection devices according to embodiments of the present disclosure.

The stabilization member and/or arms may have varying flexibility across different planes. For example, they may have omni-directional flexibility, bi-directional flexibility, or uni-directional flexibility. The stabilization member and/or arms with omni-direction flexibility may have uniform flexibility in every plane or different flexibility in different planes. Directional variation in flexibility may be achieved through shaping of the stabilization member and/or arms. For example, any one of the arms may be have a plate-like configuration similar to the arm 146 illustrated in FIG. 14*a*, such that they are more flexible in one plane than another plane, or have a circular cross-section similar to the arm 147 illustrated in FIG. 14*b*, such that they have the same flexibility in any direction.

In any of the embodiments, one or more of the arms may include resorbable elements such as resorbable collars that serve to stiffen the arms, but which are gradually resorbed within the body such that their stiffening effect gradually reduces over time. Thus, any one or more arms may have a flexibility that changes over time. This can be advantageous where increased stiffening and stabilization is required immediately post-implantation, to ensure appropriate patient recovery, but where increased flexibility and motion preservation is desirable thereafter.

Figure 15:
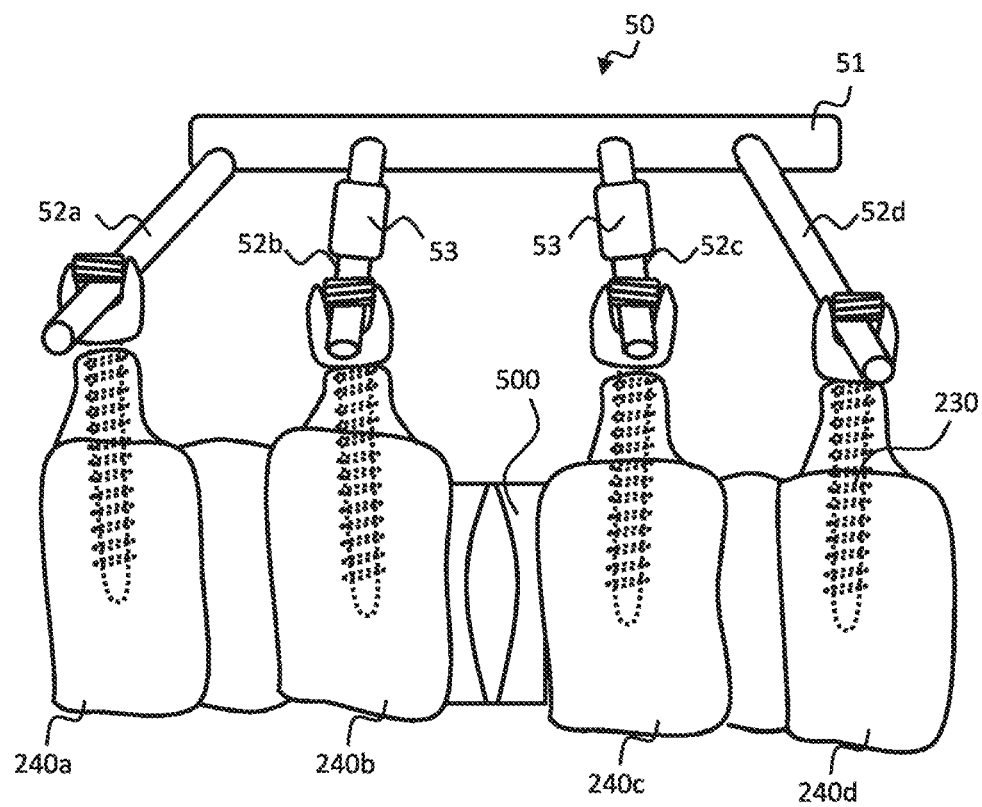
FIG. 15 shows a lateral view of a surgical connection device according to another embodiment of the present disclosure.

An example of a surgical connection device 50 including arms with resorbable elements according to an embodiment of the present disclosure is illustrated in FIG. 15. Generally, the surgical connection device 50 is designed to provide a motion preservation function, and in this instance is used in conjunction with a mobile disc replacement to provide motion preserving posterior support to a replacement disc 500. The connection device 50 includes a stabilization member 51 and a plurality of arms 52*a-d* that connect between the stabilization member and anchor points, in particular pedicle screws 230, implanted in vertebrae 240*a-d* located either side of the replacement disc 500 and on opposite lateral sides of the spine (albeit arms on one side of the spine only are represented in FIG. 15). The stabilization member 51 locates posteriorly of the pedicle screws 230. A first pair of the arms 52*b*, 52*c* connect to pedicle screws 230 implanted in first superior and inferior vertebrae 240*b*, 240*c* immediately adjacent the disc 500. A second pair of the arms 52*a*, 52*d* connect to pedicle screws 230 implanted in second superior and inferior vertebrae 240*a*, 240*d* that are immediately outside the first superior and inferior vertebrae 240*b*, 240*c*. The first pair of arms 52*b*, 52*c* each have a resorbable stiffening collar 53 mounted thereon, providing for reduced flexibility and therefore increased stiffness of the arms 52*b*, 52*c* and therefore the connection device 50, immediately adjacent the replacement disc 500. The second pair of arms 52*a*, 52*d* are substantially identical to the first pair of arms but have no stiffening collars 53. Accordingly, the second pair of arms 52*a*, 52*d* are more flexible than the first pair of arms 52*b*, 52*c*. Immediately after implantation, the connection device 50 provides for increased stiffening and stabilization adjacent the replacement disc 500, while providing greater motion-preservation function and outer vertebral levels. However, as the resorbable collars 53 are gradually resorbed over time, the first pair of arms 52*b*, 52*c* exhibit increased flexibility, increasing the motion preservation function of the entire connection device 50, when the replacement disc 500 is better integrated with the spine.

Figure 16:
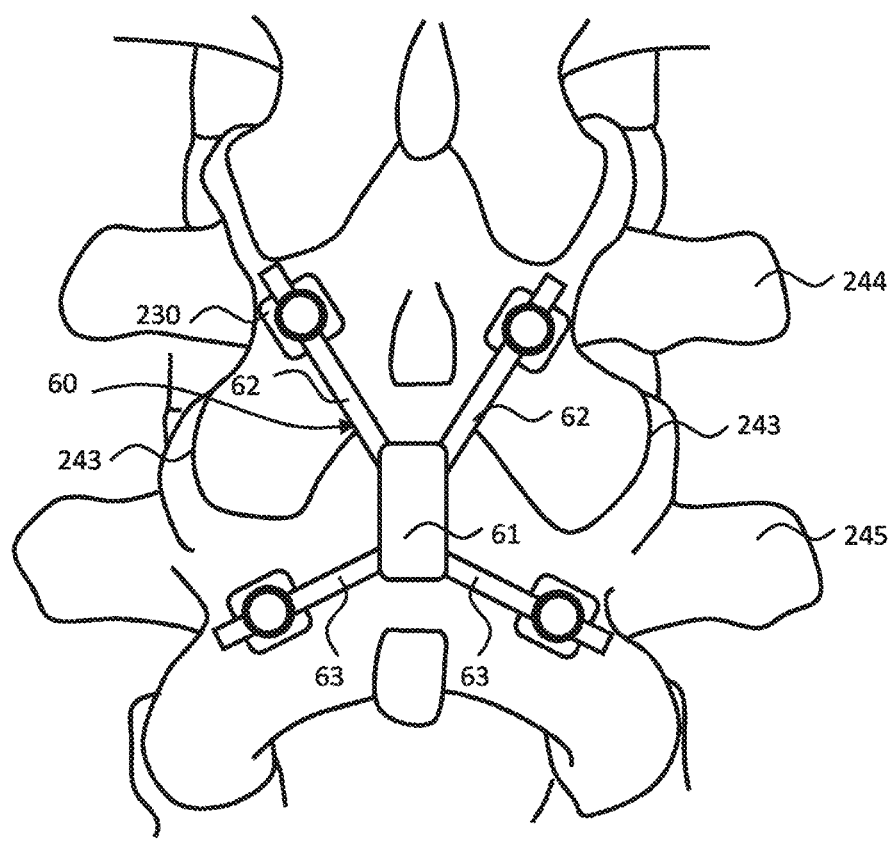
FIG. 16 shows a posterior view of a surgical connection device according to yet another embodiment of the present disclosure

In another embodiment, as shown in FIG. 16, a surgical connection device 60 is provided that is adapted to stabilize a lateral facet joint 243 of a spine. The lateral facet joint 243 being provided between an L4 vertebra 244 and an L5 vertebra 245 in this embodiment, although the connection device 60 may be used with alternative vertebrae. The connection device 60 includes a stabilization member 61 and a plurality of arms 62, 63, including a pair of first arms 61 and a pair of second arms 62. The first arms 62 are connected to anchor points, in particular pedicle screws 230, on respective lateral sides of the L4 vertebra 244 and the second arms are connected to anchor points, in particular pedicle screws 230, on respective lateral sides of the L5 vertebra 245. The stabilization member 61 is elongate along the spinal axis. The stabilization member 61 is significantly stiffer than the arms 62, 63. The flexibility of each arm 62, 63 is independently selected to allow desired stabilisation and motion preservation. The arms 62, 63 extend medially and posteriorly from their connection points with the screws 230 such that the stabilization member 61 is again positioned posteriorly of the pedicle screws 230, and above the left and right L4 nerves. A partial laminectomy of the spinous processes of the L4 and L5 vertebrae 244, 245 has been carried out to allow the stabilization member 61 to be positioned in the desired location.

Figure 17:
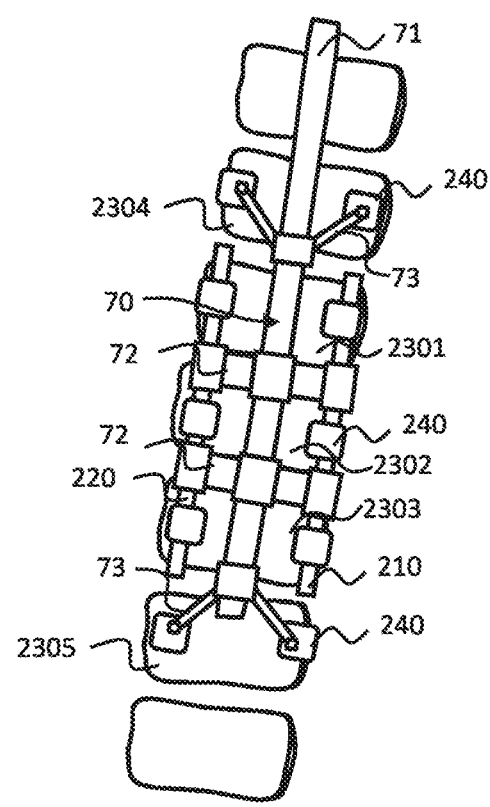
FIG. 17 shows a posterior view of a surgical connection device according to another embodiment of the present disclosure.

With reference to FIG. 17, in one embodiment a surgical connection device 70 is provided including a stabilization member 71 with a plurality of arms 72, 73. A first portion of the stabilization member 71 is connected to first and second rods 210, 220 of a first spinal portion by first arms 72. Second and third portions of the stabilization member 71, located either side of the first portion, are connected directly to anchor points 240 of second and third spinal portions by second arms 73. The first spinal portion includes three fused vertebra 2301, 2302, 2303. The second and third spinal portions are located either side of the first spinal portions and include non-fused vertebra 2304, 2305. In this embodiment, the arms 73 connecting the stabilization member 71 to the non-fused vertebrae 2304, 2305 have greater flexibility than the arms 72 connecting the stabilization member to the fused vertebrae 2301, 2302, 2303. Use of stiffer arms 72 at the fused vertebrae provides greater stability to the overall surgical connection device and rod construct without providing any adverse effect to overall motion preservation. However, the more flexible arms 73 connected to anchor points at non-fused vertebrae provide increased motion preserving stabilisation while decreasing the tendency for degeneration in those vertebral levels.

Figure 18:
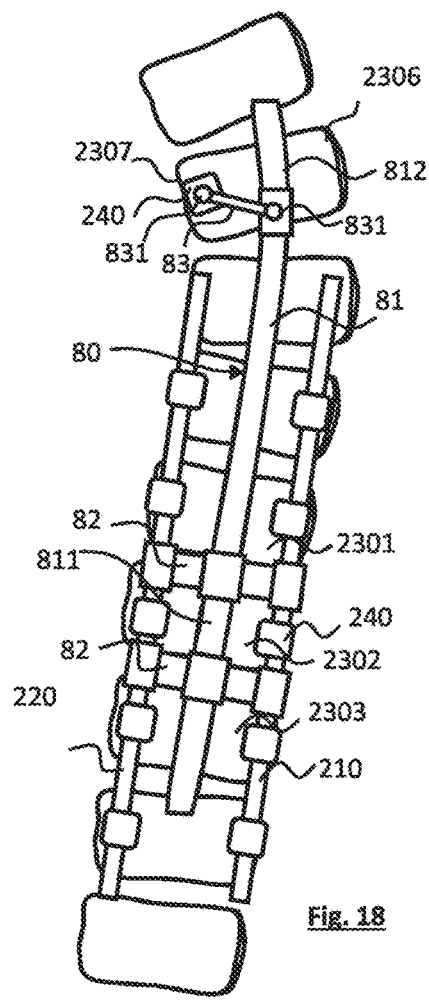
FIG. 18 shows a posterior view of a surgical connection device according to yet another embodiment of the present disclosure.

With reference to FIG. 18, in another embodiment of the present disclosure a surgical connection device 80 is provided including a stabilization member 81 and a plurality of arms 82, 83. A first portion 81 of the stabilization member 81 is connected to first and second rods 210, 220 of a first spinal portion of a scoliotic spine by anchor arms 82. A second portion 812 of the stabilization member 81, located superiorly of the first portion 811 of the stabilization member 81 in this embodiment, is connected directly to a second spinal portion by a first control arm 83. The first spinal portion includes three fused vertebra 2301, 2302, 2303. The second spinal portion is located superiorly of the first spinal portion and includes a non-fused vertebra 2306.

The first control arm 83 is adapted to control a movement of the second portion of the spine, including the non-fused superior vertebrae 2306, relative to the stabilization member 81. At the second portion 812 of the stabilization member 81, the stabilization member 81 locates at a position that is medial to a first lateral edge 2307 of the vertebra 2306. The first control arm 83 projects outwardly from the second portion 812 of the stabilization member in a direction towards the first lateral edge 2307.

The first control arm 83 is rotatable relative to the second portion 812 of the stabilization member 81 and rotatable relative to the vertebra 2306. Rotation is achieved through the provision of articulated joints 831 between the first control arm 83 and stabilization member 81 and between the first control arm 83 and the vertebra 2306.

The first control arm 83 is substantially rigid such as to maintain a fixed length while permitting movement between the vertebra 2306 and the stabilization member 81.

Figure 21:
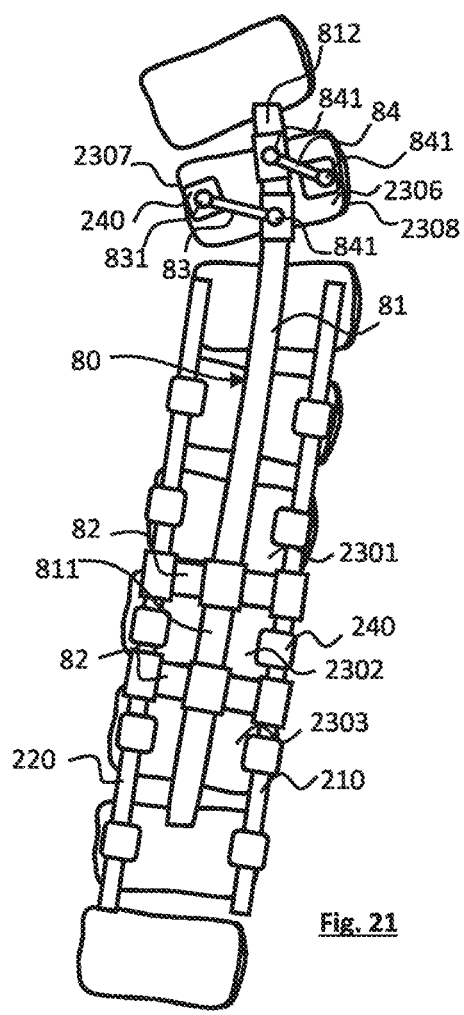
FIG. 21 shows a posterior view of a surgical connection device according to yet another embodiment of the present disclosure.

A variation of the connection device 80 is illustrated in FIG. 21. In this variation, a second control arm 84 is provided in addition to the first control arm 83. Like the first control arm 83, the second control arm 84 is also adapted to control a movement of the second portion of the spine, including the non-fused vertebrae 2306, relative to the stabilization member 81. At the second portion 812 of the stabilization member 81, the stabilization member 81 locates at a position that is also medial to a second lateral edge 2308 of the vertebra 2306. The second control arm 84 projects outwardly from the second portion 812 of the stabilization member in a direction towards the second lateral edge 2308.

The second control arm 84 is also rotatable relative to the second portion 812 of the stabilization member 81 and rotatable relative to the vertebra 2306. Rotation is again achieved through the provision of articulated joints 841 between the second control arm 84 and stabilization member 81 and between the second control arm 84 and the vertebra 2306.

By providing a first control arm 83, or first and second control arms 83, 84, which arm(s) control movement of the vertebra 2306 relative to the stabilization member 81, the surgical connection device 80 can provide for re-alignment of the scoliotic spine. Where a recipient of the surgical connection device is a child, for example, natural movement of the spine may occur as a result of growth of the spine post-implantation. The growth may be such as to move the vertebra 2306 in a direction away from the first portion of the spine including fused vertebrae 2301, 2302, 2303. However, by connecting the control arm(s) to the non-fused vertebra 2306, the direction of growth is controlled by the surgical connection device 80. Relative lengthening of the spine forces the control arm(s) 83, 84 to rotate through an arc in respective planes. The orientation of each plane is selected to drive a desired correction of the tilt and rotation of the scoliotic spine. Assisting in this process is the anchoring of the stabilization member to the fused portion of the spine.

Figures 19A, 19B:
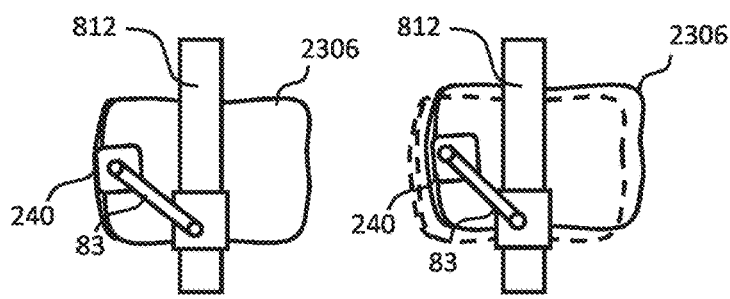
FIGS. 19a and 19b show posterior views of a portion of the surgical connection device of FIG. 18 connected to a vertebra prior to and after spinal growth, respectively.
Figures 20A, 20B:
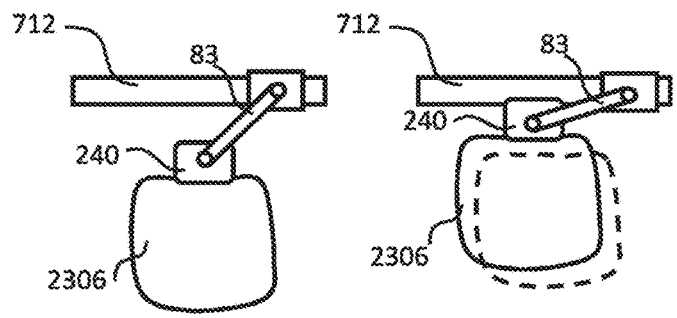
FIGS. 20a and 20b show lateral views of a portion of the surgical connection device of FIG. 18 connected to a vertebra prior to and after spinal growth, respectively.

When a single, first control arm 83 is employed, the rotation of the arm 83 forces lateral and posterior movement of the vertebra 2306, from a position as represented in FIGS. 19a and 20a to a position as represented in FIGS. 19b and 20b. (In FIGS. 19b and 20b, the dotted line indicates the prior positioning of the vertebra 2306 shown in FIGS. 19a and 20a, respectively.)

Figure 22A:
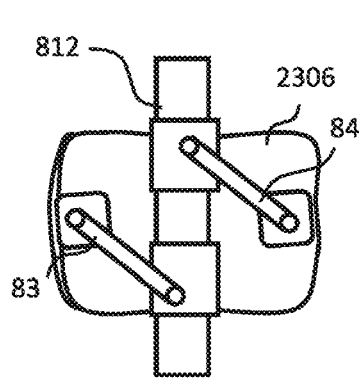
FIGS. 22a and 22b show lateral views of a portion of the surgical connection device of FIG. 21 connected to a vertebra prior to and after spinal growth, respectively.
Figure 22B:
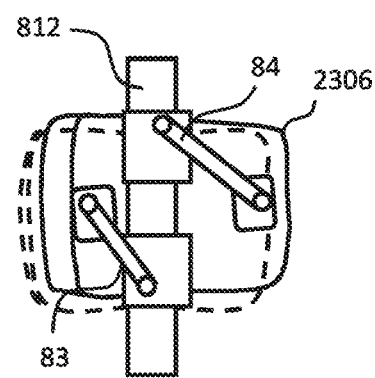

When both a first control arm 83 and a second control arm 84 are employed, the rotation of the arms 83, 84 forces lateral and posterior movement of the vertebra 2306 along with rotation of the vertebra about the spinal axis, from a position as represented in FIG. 22a to a position as represented in FIG. 22b. (In FIG. 22b, the dotted line indicates the prior positioning of the vertebra 2306 shown in FIG. 22a.)

The surgical connection device 80, while not restricting growth of the spine, may therefore force a straightening or other type of shape adjustment of the spine during growth of the spine. This can be particularly advantageous to treat scoliosis of the spine in children, although the connection device is not necessarily limited to such use. By taking the approach disclosed, growth of the spinal column may not be retarded, the need for re-operation to allow growth may be obviated or at least reduced, and correction of the spine can be achieved post-operatively and in a gradual fashion.

It will be appreciated by persons skilled in the art that numerous variations and/or modifications may be made to the above-described embodiments, without departing from the broad general scope of the present disclosure.

For example, while the device illustrated in some of the Figures is provided with compression arms projecting across a single transverse plane only, in other embodiments, compression arms may project over different transverse planes or in other directions. Two pairs of first and second compression arms may be provided, for example, located at different positions along the axis of elongation of the stabilization member.

As another example, in any one of the embodiments further arms of rods may be connected to the arms, e.g., the traction or compression arms, in a longitudinally arranged manner. This may further stabilise the construct and provide further stiffening or induction of tension. The further arms or rods may run substantially parallel to the first and second rods and to the stabilisation device, for a portion or whole of the construct. This may be particularly advantageous where the first and second rods (connected between the anchor points) are excluded, in order to increase rigidity of the construct.

As yet another example, the device may comprise additional arms that are connectable to the stabilisation member where longer constructs are desired. For example, first and second compression arms may be integral to the system, but for longer constructs further compression arms may be also be included or selectively introduced by the surgeon.

The present embodiments are, therefore, to be considered in all respects as illustrative and not restrictive.

The invention claimed is:

1. A surgical connection device for a spine, wherein at least one first spinal rod is configured to fix a group of first vertebrae together at a first lateral side of the spine and at least one second spinal rod is configured to fix the group of first vertebrae together at a second lateral side of the spine, the surgical connection device comprising:
   an elongate stabilization member;
   one or more anchor arms, each of the one or more anchor arms having a first end connected to a first portion of the elongate stabilization member and a second end configured to connect to the group of first vertebrae; and
   one or more first control arms each having a first end connected to a second portion of the elongate stabilization member and a second end configured to connect to at least one second vertebra of the spine,
   wherein the one or more first control arms are rotatable to provide dynamic stabilization of the at least one second vertebra, and
   wherein the first end of the one or more first control arms connects to the second portion of the elongate stabilization member at a connection position that is posterior of a plane extending through the at least one first and the at least one second spinal rods and medial of a first axis extending longitudinally through the at least one first rod and a second axis extending longitudinally through the at least one second rod.

2. The surgical connection device of claim 1, wherein the one or more first control arms are flexible to enable the one or more first control arms to rotate.

3. The surgical connection device of claim 2, wherein at least one of the first control arms is more flexible than at least one of the one or more anchor arms.

4. The surgical connection device of claim 1, wherein at least one of the one or more anchor arms is rigid.

5. The surgical connection device of claim 1, wherein the one or more first control arms are connected to the second portion of the elongate stabilization member via an articulated joint to enable the one or more first control arms to rotate.

6. The surgical connection device of claim 1, wherein the one or more first control arms are configured to connect to the at least one second vertebra via an articulated joint.

7. The surgical connection device of claim 1, wherein the second portion of the elongate stabilization member is positioned superiorly of the first portion of the elongate stabilization member.

8. The surgical connection device of claim 1, wherein the second end of at least one of the one or more first control arms is configured to connect to the at least one second vertebra of the spine that is positioned superiorly of the group of first vertebrae.

9. The surgical connection device of claim 1, wherein the second portion of the elongate stabilization member is positioned inferiorly of the first portion of the elongate stabilization member.

10. The surgical connection device of claim 1, wherein the second end of at least one of the first control arms is configured to connect to the at least one second vertebra of the spine that is positioned inferiorly of the group of first vertebrae.

11. The surgical connection device of claim 1, comprising at least two of the one or more first control arms.

12. The surgical connection device of claim 11, wherein the second ends of the at least two of the one or more first control arms are configured to connect to opposing lateral sides of the at least one second vertebra.

13. The surgical connection device of claim 1, further comprising one or more second control arms each having a first end connected to a third portion of the elongate stabilization member and a second end configured to connect to at least one third vertebra of the spine, wherein the one or more second control arms are rotatable to provide dynamic stabilization of the at least one third vertebra, the at least one third vertebra being at an opposite side of the group of first vertebrae to the at least one second vertebra.

14. The surgical connection device of claim 13, wherein the one or more first control arms apply a lordotic or kyphotic bias to the at least one second vertebra and the one or more second control arms apply a lordotic or kyphotic bias to the at least one third vertebra.

15. The surgical connection device of claim 1, wherein the one or more anchor arms are configured to fix the position of the elongate stabilization member relative to the group of first vertebrae of the spine such that elongate stabilization member extends along the spine.

16. The surgical connection device of claim 1, wherein the one or more anchor arms are configured to fix the position of the elongate stabilization member relative to the group of first vertebrae of the spine such that elongate stabilization member extends parallel to the spine.

17. The surgical connection device of claim 1, wherein the second end of the one or more anchor arms is configured to connect to the group of first vertebrae by the second end of the one or more anchor arms being connected to at least one of the at least one first and at least one second spinal rods.

18. The surgical connection device of claim 17, wherein the one or more anchor arms comprise at least a first anchor arm and a second anchor arm, the first anchor arm having a first end connected to the first portion of the elongate stabilization member and a second end configured to connect to the at least one first spinal rod, and the second anchor arm having a first end connected to the first portion of the elongate stabilization member and a second end configured to connect to the at least one second spinal rod.

19. The surgical connection device of claim 1, wherein the second end of the one or more anchor arms is configured to connect to the group of first vertebrae by the second end of the one or more anchor arms being connected to a screw that is fixed to a first vertebra of the group of first vertebrae.

20. The surgical connection device of claim 1, wherein the one or more first control arms apply a lordotic or kyphotic bias to the second vertebra.

21. The surgical connection device of claim 1, wherein the one or more first control arms comprise a plurality of first control arms each having a second end configured to connect to a different first vertebrae, and wherein the plurality of first control arms each have a different stiffness.

22. The surgical connection device of claim 21, wherein the plurality of first control arms have differing stiffness by virtue of the plurality of first control arms being formed of different materials, having different diameters and/or having different shapes.

23. The surgical connection device of claim 1, wherein the elongate stabilization member is configured to be positioned:
   at least 5 mm posteriorly of a plane extending through the at least one first and the at least one second spinal rods; or
   at least 10 mm posteriorly of a plane extending through the at least one first and the at least one second spinal rods; or
   between 5 mm and 25 mm posteriorly of a plane extending through the at least one first and the at least one second spinal rods; or
   between 5 mm and 25 mm posteriorly of a plane extending through the at least one first and the at least one second spinal rods; or
   between 5 mm and 35 mm posteriorly of a plane extending through the at least one first and the at least one second spinal rods.

* * * * *